(12) United States Patent
Olsson et al.

(10) Patent No.: US 11,939,433 B2
(45) Date of Patent: *Mar. 26, 2024

(54) METHOD FOR PREPARING ACYLATED CROSSLINKED GLYCOSAMINOGLYCANS

(71) Applicant: Galderma Holding SA, Zug (CH)

(72) Inventors: Johan Olsson, Bromma (SE); Craig Steven Harris, Biot (FR)

(73) Assignee: GALDERMA HOLDING S.A., Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/208,527

(22) Filed: Jun. 12, 2023

(65) Prior Publication Data

US 2023/0323041 A1    Oct. 12, 2023

Related U.S. Application Data

(63) Continuation of application No. 17/129,366, filed on Dec. 21, 2020, now Pat. No. 11,708,461, which is a
(Continued)

(30) Foreign Application Priority Data

Dec. 29, 2015 (EP) .................................. 15202944
May 31, 2016 (EP) .................................. 16172225
(Continued)

(51) Int. Cl.
*C08J 3/075* (2006.01)
*A61K 8/04* (2006.01)
(Continued)

(52) U.S. Cl.
CPC ............... *C08J 3/075* (2013.01); *A61K 8/042* (2013.01); *A61K 8/73* (2013.01); *A61K 8/735* (2013.01);
(Continued)

(58) Field of Classification Search
CPC .......... C08J 2305/08; C08J 3/24; C08J 3/246; C08B 37/0072
See application file for complete search history.

(56) References Cited

U.S. PATENT DOCUMENTS 5,731,298 A   3/1998   Reinmuller
6,132,750 A   10/2000  Perrier et al.
(Continued)

FOREIGN PATENT DOCUMENTS

CN    1529716 A   9/2004
CN    1570128 A   1/2005
(Continued)

OTHER PUBLICATIONS

Ahmed, "Hydrogel: Preparation, characterization, and applications: A review" Journal of Advanced Research vol. 6 pp. 105-121 (Year: 2015).*
(Continued)

*Primary Examiner* — Eric Olson
(74) *Attorney, Agent, or Firm* — Sunit Talapatra; Foley & Lardner LLP (57) ABSTRACT

A method of preparing a hydrogel product including crosslinked glycosaminoglycan molecules, said method including: i) providing a glycosaminoglycan crosslinked by amide bonds, wherein the crosslinked glycosaminoglycans include residual amine groups; and ii) acylating residual amine groups of the crosslinked glycosaminoglycans provided in i) to form acylated crosslinked glycosaminoglycans.

20 Claims, 2 Drawing Sheets

Related U.S. Application Data continuation of application No. 16/066,985, filed as application No. PCT/EP2016/082778 on Dec. 28, 2016, now Pat. No. 10,899,894.

(30) Foreign Application Priority Data

| | | | |
|---|---|---|---|
| May 31, 2016 | (EP) | ................................ | 16172241 |
| May 31, 2016 | (EP) | ................................ | 16172254 |

(51) Int. Cl.

| | |
|---|---|
| A61K 8/73 | (2006.01) |
| A61K 9/00 | (2006.01) |
| A61Q 19/00 | (2006.01) |
| C07C 209/62 | (2006.01) |
| C07C 213/00 | (2006.01) |
| C07C 269/06 | (2006.01) |
| C07F 7/08 | (2006.01) |
| C08B 37/00 | (2006.01) |
| C08B 37/08 | (2006.01) |
| C08J 3/24 | (2006.01) |
| C08J 7/14 | (2006.01) |
| C08K 5/09 | (2006.01) |
| C08L 5/00 | (2006.01) |
| C08L 5/08 | (2006.01) |

(52) U.S. Cl.
CPC ............ *A61K 9/0019* (2013.01); *A61Q 19/00* (2013.01); *C07C 209/62* (2013.01); *C07C 213/00* (2013.01); *C07C 269/06* (2013.01); *C07F 7/083* (2013.01); *C08B 37/0063* (2013.01); *C08B 37/0069* (2013.01); *C08B 37/0072* (2013.01); *C08J 3/24* (2013.01); *C08J 7/14* (2013.01); *C08K 5/09* (2013.01); *C08L 5/00* (2013.01); *C08L 5/08* (2013.01); *C07C 2603/18* (2017.05); *C08J 2305/00* (2013.01); *C08J 2305/08* (2013.01)

(56) References Cited

U.S. PATENT DOCUMENTS

| | | | |
|---|---|---|---|
| 6,495,314 B1 | 12/2002 | Kent et al. | |
| 6,703,444 B2 | 3/2004 | Zhao et al. | |
| 6,831,172 B1 | 12/2004 | Barbucci et al. | |
| 7,731,758 B2 | 6/2010 | Asius et al. | |
| 8,414,657 B2 | 4/2013 | Asius et al. | |
| 8,858,999 B2 | 10/2014 | Giammona et al. | |
| 8,887,243 B2 | 11/2014 | Thomson et al. | |
| 10,105,197 B1 | 10/2018 | Colon | |
| 10,889,894 B2 | 1/2021 | Hwung et al. | |
| 11,198,765 B2 | 12/2021 | Olsson et al. | |
| 11,254,792 B2 * | 2/2022 | Olsson | ............... C08B 37/0072 |
| 11,530,301 B2 | 12/2022 | Mojarradi et al. | |
| 11,708,461 B2 * | 7/2023 | Olsson | ..................... C08K 5/09 514/54 |
| 2003/0093157 A1 | 5/2003 | Casares et al. | |
| 2004/0014960 A1 | 1/2004 | Moon et al. | |
| 2004/0072793 A1 | 4/2004 | Aeschlimann et al. | |
| 2004/0219630 A1 | 11/2004 | Tsubouchi | |
| 2006/0166928 A1 | 7/2006 | Moon et al. | |
| 2007/0053987 A1 | 3/2007 | Bayer et al. | |
| 2007/0065481 A1 | 3/2007 | Chudzik et al. | |
| 2007/0066816 A1 | 3/2007 | Tsai et al. | |
| 2009/0011045 A1 | 1/2009 | Mertin et al. | |
| 2010/0136070 A1 | 6/2010 | Dobak et al. | |
| 2010/0255068 A1 | 10/2010 | Stroumpoulis et al. | |
| 2012/0231046 A1 | 9/2012 | Asius et al. | |
| 2013/0085187 A1 | 4/2013 | Kim et al. | |
| 2013/0338352 A1 | 12/2013 | Yasugi et al. | |
| 2014/0094568 A1 | 4/2014 | James et al. | |
| 2015/0045573 A1 | 2/2015 | Cheng et al. | |
| 2016/0106718 A1 | 4/2016 | Gupta | |
| 2019/0016830 A1 | 1/2019 | Olsson et al. | |
| 2019/0023812 A1 | 1/2019 | Mojarradi et al. | |
| 2019/0023855 A1 | 1/2019 | Olsson et al. | |

FOREIGN PATENT DOCUMENTS

| | | |
|---|---|---|
| CN | 1694903 A | 11/2005 |
| CN | 102952281 | 3/2013 |
| CN | 103038339 A | 4/2013 |
| CN | 103788222 A | 5/2014 |
| CN | 104194066 A | 12/2014 |
| DE | 44 39 575 A1 | 5/1996 |
| EP | 0 224 987 A2 | 6/1987 |
| EP | 0 903 152 A2 | 3/1999 |
| EP | 1 837 347 A1 | 9/2007 |
| EP | 2 609 924 A1 | 7/2013 |
| EP | 2 682 409 A1 | 1/2014 |
| EP | 2 727 597 A1 | 5/2014 |
| EP | 3 020 733 A1 | 5/2016 |
| EP | 3 397 651 A1 | 11/2018 |
| JP | S62-265998 A | 11/1987 |
| JP | H11-152234 A | 6/1999 |
| JP | 2002-519481 A | 7/2002 |
| JP | 2004-507588 A | 3/2004 |
| JP | 2004-511588 A | 4/2004 |
| JP | 2006-505633 A | 2/2006 |
| JP | 2009-507103 A | 2/2009 |
| JP | 2014-531433 A | 11/2014 |
| JP | 2015-537078 A | 12/2015 |
| WO | WO-97/11958 A1 | 4/1997 |
| WO | WO-00/46252 A1 | 8/2000 |
| WO | WO-00/46253 A1 | 8/2000 |
| WO | WO-02/18450 A1 | 3/2002 |
| WO | WO-02/30990 A1 | 4/2002 |
| WO | WO-02/081739 A2 | 10/2002 |
| WO | WO-02/082078 A2 | 10/2002 |
| WO | WO-2004/011503 A1 | 2/2004 |
| WO | WO-2004/057008 A1 | 7/2004 |
| WO | WO-2007/026362 A2 | 3/2007 |
| WO | WO-2013/086024 A2 | 6/2013 |
| WO | WO-2014/072330 A1 | 5/2014 |
| WO | WO-2015/021092 | 2/2015 |
| WO | WO-2015/034436 | 3/2015 |
| WO | WO-2015/181365 A1 | 12/2015 |
| WO | WO-2015/181369 A1 | 12/2015 |
| WO | WO-2017/114861 | 7/2017 |
| WO | WO-2017/114864 A1 | 7/2017 |
| WO | WO-2017/114865 | 7/2017 |
| WO | WO-2017/114867 A1 | 7/2017 |
| WO | WO-2019/001784 A1 | 1/2019 |
| WO | WO-2019/002368 A1 | 1/2019 |
| WO | WO-2019/002370 A1 | 1/2019 |

OTHER PUBLICATIONS

Borke et al., "Optimized triazine-mediated amidation for efficient and controlled functionalization of hyaluronic acid", Carbohydrate Polymers 116, Apr. 19, 2014, pp. 42-50.

Canova-Davis et al., "Chemical heterogeneity as a result of hydroxylamine cleavage of a fusion protein of human insulin-like growth factor I", Biochem. J., vol. 285, Jan. 6, 1992, pp. 207-213.

Crimmins et al., "Chemical Cleavage of Proteins in Solution", Current Protocols in Protein Science, 2005, pp. 11.4.1-11.4.11.

D'Este et al., "A systematic analysis of DMTMM vs EDC/NHS for ligation of amines to Hyaluronan in water", Carbohydrate Polymers 108, Mar. 14, 2014, pp. 239-246.

Gomez-Reyes et al., "Metal-catalyzed hydroxylaminolysis of unactivated amide and peptide bonds," Org. Biomol. Chem., vol. 1, Feb. 11, 2003, pp. 866-872.

Gupta et al., "Hydrogels for wound healing applications", Biomedical Hydrogels Biochemistry, 2011, pp. 184-227.

International Search Report (PCT/ISA/210) dated Jul. 31, 2017, by the European Patent Office as the International Searching Authority for International Application No. PCT/EP2017/063029 (5 pages).

(56) References Cited

OTHER PUBLICATIONS

International Search Report (PCT/ISA/210) dated Feb. 20, 2017, by the European Patent Office as the International Searching Authority for International Application No. PCT/EP2016/082778 (4 pages).
International Search Report (PCT/ISA/210) dated Feb. 20, 2017, by the European Patent Office as the International Searching Authority for International Application No. PCT/EP2016/082781 (4 pages).
International Search Report (PCT/ISA/210) dated Feb. 22, 2017, by the European Patent Office as the International Searching Authority for International Application No. PCT/EP2016/082783 (3 pages).
International Search Report (PCT/ISA/210) dated Feb. 23, 2017, by the European Patent Office as the International Searching Authority for International Application No. PCT/EP2016/082774 (5 pages).
International Search Report (PCT/ISA/210) dated May 10, 2017, by the European Patent Office as the International Searching Authority for International Application No. PCT/EP2016/082770 (5 pages).
International Search Report and Written Opinion on PCT Appl. Ser. No. PCT/IB2020/061336 dated Mar. 1, 2021 (9 pages).
International Search Report and Written Opinion on PCT PCT/IB2020/060066 dated Jan. 12, 2021 (14 pages).
Kurita et al., "Synthetic Carbohydrate Polymers Containing Trehalose Residues in the Main Chain: Preparation and Characteristic Properties," Macromolecules, vol. 27, No. 26, Jun. 27, 1994, pp. 7544-7549.
Maleki et al.; "Characterization of the chemical degradation of hyaluronic acid during chemical gelation in the presence of different cross-linker agents", Carbohydrate Research, vol. 342, Sep. 6, 2007, pp. 2776-2792.
Oladunni et al., "Chemically Modified N-Acylated Hyaluronan Fragments Modulate Proinflammatory Cytokine Production by Stimulated Human Macrophages," The Journal of Biological Chemistry, vol. 289, No. 36, Sep. 5, 2014. pp. 24779-24791.
Olson et al., "Specificity of Fatty Acid Acylation of Cellular Proteins," The Journal of Biological Chemistry, vol. 260, No. 6, Mar. 25, 1985, pp. 3784-3790.

Rydergren, "Chemical Modifications of Hyaluronan using DMTMM-Activated Amidation," Uppsala Universitet, Aug. 2013, pp. 1-30. (English Abstract only).
Schante et al., "Chemical modification of hyaluronic acid for the synthesis of derivatives for a broad range of biomedical applications", Carbohydrate Polymers 85, Mar. 21, 2011, pp. 469-489.
Tomihata et al., "Crosslinking of hyaluronic acid with water-soluble carbodiimide," Research Center for Biomedical Engineering, 1995-1996, pp. 243-251.
Tsigos et al., "Chitin deacetylases: new, versatile tools in biotechnology", Trends in Biotechnology, Elsevier Publications, Cambridge, vol. 18, No. 7, Jul. 1, 2000, XP004908536, pp. 305-312.
Werner et al., "Regulation of Wound Healing by Growth Factors and Cytokines", Physiol Rev, vol. 83, Jul. 2003, pp. 835-870.
Written Opinion (PCT/ISA/210) dated Jul. 31, 2017 by the European Patent Office as the International Searching Authority for International Application No. PCT/EP2017/063029 (6 pages).
Written Opinion (PCT/ISA/237) dated Feb. 20, 2017, by the European Patent Office as the International Searching Authority for International Application No. PCT/EP2016/082778 (5 pages).
Written Opinion (PCT/ISA/237) dated Feb. 22, 2017, by the European Patent Office as the International Searching Authority for International Application No. PCT/EP2016/082783 (4 pages).
Written Opinion (PCT/ISA/237) dated Feb. 23, 2017, by the European Patent Office as the International Searching Authority for International Application No. PCT/EP2016/082774 (7 pages).
Written Opinion (PCT/ISA/237) dated May 10, 2017, by the European Patent Office as the International Searching Authority for International Application No. PCT/EP2016/082770 (6 pages).
Zhu et al., "Selective cleavage of isoaspartyl peptide bonds by hydroxylamine after methyltransferase priming", Analytical Biochemistry, Elsevier, Amsterdam, NL, vol. 364, No. 1, Mar. 31, 2007, XP022005959, pp. 1-7.

\* cited by examiner

METHOD FOR PREPARING ACYLATED CROSSLINKED GLYCOSAMINOGLYCANS

CROSS-REFERENCE TO RELATED APPLICATIONS

The present application is a Continuation application of U.S. patent application Ser. No. 17/129,366, filed Dec. 21, 2020, which application is a Continuation application of U.S. patent application Ser. No. 16/066,985, filed Jun. 28, 2018, which is a National Stage Application of International Application No. PCT/EP2016/082778, filed on Dec. 28, 2016, which claims the benefit of priority to EP Patent Application No. 15202944.3, filed on Dec. 29, 2015; EP Patent Application No. 16172254.1, filed on May 31, 2016; EP Patent Application No. 16172225.1, filed on May 31, 2016; and EP Patent Application No. 16172241.8, filed on May 31, 2016; the entirety of each and every one of the aforementioned applications is herein expressly incorporated by reference.

TECHNICAL FIELD OF THE INVENTION

The present invention relates to the field of hydrogels containing crosslinked polysaccharides and the use of such hydrogels in medical and/or cosmetic applications. More specifically, the present invention is concerned with hydrogels made of crosslinked glycosaminoglycans, particularly crosslinked hyaluronic acid, chondroitin or chondroitin sulfate.

BACKGROUND OF THE INVENTION

Water-absorbing gels, or hydrogels, are widely used in the biomedical field. They are generally prepared by chemical crosslinking of polymers to infinite networks. While many polysaccharides absorb water until they are completely dissolved, crosslinked gels of the same polysaccharides can typically absorb a certain amount of water until they are saturated, i.e. they have a finite liquid retention capacity, or swelling degree.

Hyaluronic acid, chondroitin and chondroitin sulfate are well-known biocompatible polymers. They are naturally occurring polysaccharides belonging to the group of glycosaminoglycans (GAGs). All GAGs are negatively charged heteropolysaccharide chains which have a capacity to absorb large amounts of water.

Hyaluronic acid (HA) is one of the most widely used biocompatible polymers for medical and cosmetic use. HA is a naturally occurring polysaccharide belonging to the group of glycosaminoglycans (GAGs). Hyaluronic acid and products derived from hyaluronic acid are widely used in the biomedical and cosmetic fields, for instance during viscosurgery and as a dermal filler.

Chondroitin sulfate (CS) is a highly abundant GAG found in the connective tissues of mammals where it, together with other sulfated GAGs, is bound to proteins as part proteoglycans. It has previously been shown that hydrogels containing CS successfully can be used in biomedical applications due to their resemblance to the natural extra cellular matrix (Lauder, R. M., Complement Ther Med 17: 56-62, 2009). Chondroitin sulfate is also used in the treatment of osteoarthritis, e.g. as a dietary supplement.

Crosslinking of the glycosaminoglycans prolongs the duration of the degradable polymers that make up the network, which is useful in may application. However, the crosslinking can also reduce the native properties of the glycosaminoglycans. Hence, it is typically desired to maintain a low degree of modification by efficient crosslinking to conserve the native properties and effects of the glycosaminoglycan itself.

SUMMARY OF THE INVENTION

It is an object of the present invention to provide a hydrogel having a glycosaminoglycan (GAG) as the swellable polymer.

It is a further object of the present invention to provide a method for crosslinking GAG molecules resulting in a hydrogel product based entirely on carbohydrate type structures.

It is also an object of the present invention to provide a method for preparing hydrogels of GAG molecules by mild and efficient routes.

According to aspects illustrated herein, there is provided method of preparing a hydrogel product comprising crosslinked glycosaminoglycan molecules, said method comprising:
  i) providing a glycosaminoglycan crosslinked by amide bonds, wherein the crosslinked glycosaminoglycans comprise residual amine groups; and
  ii) acylating residual amine groups of the crosslinked glycosaminoglycans provided in i) to form acylated crosslinked glycosaminoglycans.

According to some embodiments, i) comprises the steps:
  a) providing a solution comprising an at least partially deacetylated glycosaminoglycan and optionally a second glycosaminoglycan;
  b) activating carboxyl groups on the at least partially deacetylated glycosaminoglycan and/or the optional second glycosaminoglycan with a coupling agent, to form activated glycosaminoglycans;
  c) crosslinking the activated glycosaminoglycans via their activated carboxyl groups using amino groups of the at least partially deacetylated glycosaminoglycans to provide glycosaminoglycans crosslinked by amide bonds.

The present invention is based on the inventive realization that acylation, for example acetylation, of residual free amine groups in a hydrogel product comprising amide crosslinked glycosaminoglycan molecules can be used to modify the mechanical properties of the hydrogel product. Without wishing to be bound to any specific scientific explanation, it is contemplated that acylation of the free amine groups can reduce the formation of zwitterionic complexes acting as additional crosslinks in the hydrogel product, thereby resulting in the formation of a softer gel.

Furthermore, acylation of residual free amine groups in a hydrogel product comprising amide crosslinked glycosaminoglycan molecules can also be used to connect other functional groups or active compounds to the hydrogel product. For example, amino acid derivatives, bioactive peptides and drug substances that have a carbonyl functionality may be connected to the residual free amine groups of the hydrogel product using coupling protocols known in the art.

According to some embodiments, the step ii) comprises acetylating residual amine groups of the crosslinked glycosaminoglycans provided in step i) to form acetylated crosslinked glycosaminoglycans. Glycosaminoglycans in their native form are N-acetylated. Acetylation of free amine groups in a hydrogel product may therefore be expected to produce a hydrogel product more similar to the native glycosaminoglycans.

By the term "at least partial deacetylation" as used herein as used herein with reference to the glycosaminoglycan, we mean that at least some of the N-acetyl groups of a glycosaminoglycan comprising N-acetyl groups are cleaved off, resulting in the formation of free amine groups in the glycosaminoglycan. By the term "at least partial deacetylation" as used herein, we mean that a significant portion of the N-acetyl groups of the glycosaminoglycan, particularly at least 1%, preferably at least 2%, at least 3%, at least 4%, or at least 5%, of the N-acetyl groups of the glycosaminoglycan are converted to free amine groups. More preferably, at least 3% of the N-acetyl groups of the glycosaminoglycan are converted to free amine groups.

By the term "at least partially deacetylated" as used herein with reference to the glycosaminoglycan, we mean a glycosaminoglycan comprising N-acetyl groups in which at least some of the N-acetyl groups have been cleaved off, resulting in the formation of free amine groups in the glycosaminoglycan. By "at least partially deacetylated" as used herein, we mean that a significant portion of the N-acetyl groups of the glycosaminoglycan, particularly at least 1%, preferably at least 2%, at least 3%, at least 4%, at least 5%, of the N-acetyl groups of the glycosaminoglycan have been converted to free amine groups. More preferably, at least 3% of the N-acetyl groups of the glycosaminoglycan have been converted to free amine groups.

According to some embodiments, the at least partially deacetylated glycosaminoglycan employed in step a) of the method of preparing a hydrogel product is a deacetylated glycosaminoglycan having a degree of acetylation of 99% or less, preferably 98% or less, preferably 97% or less, preferably 96% or less, preferably 95% or less, preferably 94% or less, preferably 93% or less, and a weight average molecular weight of 0.1 MDa or more, preferably 0.5 MDa or more.

According to some embodiments, the at least partially deacetylated glycosaminoglycan employed in step a) of the method of preparing a hydrogel product is a deacetylated glycosaminoglycan selected from the group consisting of deacetylated sulfated or non-sulfated glycosaminoglycans such as deacetylated hyaluronan, deacetylated chondroitin, deacetylated chondroitin sulphate, deacetylated heparan sulphate, deacetylated heparosan, deacetylated heparin, deacetylated dermatan sulphate and deacetylated keratan sulphate. Preferably, the at least partially deacetylated glycosaminoglycan employed in step a) of the method of preparing a hydrogel product is selected from the group consisting of deacetylated hyaluronic acid, deacetylated chondroitin and deacetylated chondroitin sulfate, and mixtures thereof. Preferably, the at least partially deacetylated glycosaminoglycan employed in step a) of the method of preparing a hydrogel product is deacetylated hyaluronic acid.

According to some embodiments, the optional second glycosaminoglycan employed in step a) of the method of preparing a hydrogel product is a glycosaminoglycan selected from the group consisting of sulfated or non-sulfated glycosaminoglycans such as hyaluronan, chondroitin, chondroitin sulphate, heparan sulphate, heparosan, heparin, dermatan sulphate and keratan sulphate. Preferably, the optional second glycosaminoglycan employed in step a) of the method of preparing a hydrogel product is selected from the group consisting of hyaluronic acid, chondroitin and chondroitin sulfate, and mixtures thereof. Preferably, the optional second glycosaminoglycan employed in step a) of the method of preparing a hydrogel product is hyaluronic acid.

Hyaluronic acid is one of the most widely used biocompatible polymers for medical use. Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Water-absorbing gels, or hydrogels, are widely used in the biomedical field. They are generally prepared by chemical crosslinking of polymers to infinite networks. While native hyaluronic acid and certain crosslinked hyaluronic acid products absorb water until they are completely dissolved, crosslinked hyaluronic acid gels typically absorb a certain amount of water until they are saturated, i.e. they have a finite liquid retention capacity, or swelling degree.

Since hyaluronic acid is present with identical chemical structure except for its molecular mass in most living organisms, it gives a minimum of foreign body reactions and allows for advanced medical uses. Crosslinking and/or other modifications of the hyaluronic acid molecule is typically necessary to improve its duration in vivo. Furthermore, such modifications affect the liquid retention capacity of the hyaluronic acid molecule. As a consequence thereof, hyaluronic acid has been the subject of many modification attempts.

In preferred embodiments, the glycosaminoglycan is a native glycosaminoglycan. The glycosaminoglycan used in connection with the invention is preferably a naturally occurring glycosaminoglycan. The glycosaminoglycan is preferably used in its native state. I.e., the chemical structure of the glycosaminoglycan has preferably not been altered or modified by addition of functional groups or the like. Using the glycosaminoglycan in its native state is preferred because this will afford a crosslinked structure more closely resembling the natural molecules, which conserves the native properties and effects of the glycosaminoglycan itself, and can minimize the immune response when the crosslinked glycosaminoglycan is introduced into the body.

The method of preparing a hydrogel product involves crosslinking of glycosaminoglycan molecules by covalent bonds, preferably amide bonds, typically using an activating agent for the carboxyl groups on the glycosaminoglycan molecule backbone and amino groups of an at least partially deacetylated glycosaminoglycan. Crosslinking according to the inventive method can be achieved by mild and efficient routes resulting in high yields with minimal degradation of the glycosaminoglycan molecules.

Crosslinking glycosaminoglycans directly via formation of amide bonds between amino and carboxyl groups present on the glycosaminoglycans provides a hydrogel product based entirely on carbohydrate type structures. This could reduce the disturbance of the native properties of the glycosaminoglycans often caused by crosslinking with non-saccharide based crosslinkers.

According to some embodiments, the activation step b) and the crosslinking step c) occur simultaneously. In other embodiments, the activation step b) occurs prior to and separately from the crosslinking step c).

According to some embodiments, the method further comprises providing particles of the crosslinked glycosaminoglycans, having an average size in the range of 0.01-5 mm, preferably 0.1-0.8 mm.

According to some embodiments, the coupling agent of step b) is a peptide coupling reagent.

According to some embodiments, the peptide coupling reagent is selected from the group consisting of triazine-based coupling reagents, carbodiimide coupling reagents, imidazolium-derived coupling reagents, Oxyma and COMU.

According to some embodiments, the peptide coupling reagent is a triazine-based coupling reagent. According to some embodiments, the triazine-based coupling reagent is selected from the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT). According to some embodiments, the triazine-based coupling reagent is DMTMM.

According to some embodiments, the peptide coupling reagent is a carbodiimide coupling reagent. According to some embodiments, the carbodiimide coupling reagent is N-(3-dimethylaminopropyl)-N'-ethylcarbodiimide (EDC) combined with N-hydroxysuccinimide (NHS).

Another preferred peptide coupling reagent is 2-chloro-1-methylpyridinium iodide (CMPI).

According to some embodiments, the step ii) comprises allowing the crosslinked glycosaminoglycans provided in step i) to react with an acylating agent under reaction conditions suitable to form acylated crosslinked glycosaminoglycans.

According to some embodiments, the step ii) comprises allowing the crosslinked glycosaminoglycans provided in step i) to react with an acetylating agent under reaction conditions suitable to form acetylated crosslinked glycosaminoglycans.

According to some embodiments, the acetylating agent is selected from the group consisting of acetic anhydride, isopropenyl acetate and pre-activated ester of acetic acid.

According to some embodiments, the method further comprises the step: iii) subjecting the crosslinked glycosaminoglycans provided in step i) or ii) to alkaline treatment to hydrolyze ester crosslinks formed as byproducts during the amide crosslinking.

According to some embodiments, the step iii) comprises subjecting the crosslinked glycosaminoglycans provided in step i) or ii) to alkaline treatment comprises contacting the crosslinked glycosaminoglycans with an alkaline solution, preferably an NaOH or KOH solution, having a pH in the range of 12-14, preferably a pH in the range of 12-14, for 0.5-4 hours, preferably for 0.5-2 hours.

According to some embodiments, the alkaline treatment step iii) is performed at a temperature in the range of 0-60° C., preferably in the range of 10-30° C.

According to some embodiments, the at least partially deacetylated glycosaminoglycan provided in step a) is provided by a method for at least partial deacetylation of a glycosaminoglycan, comprising:
  a1) providing a glycosaminoglycan comprising acetyl groups;
  a2) allowing the glycosaminoglycan comprising acetyl groups to react with hydroxylamine (NH$_2$OH) or a salt thereof at a temperature of 100° C. or less for 2-200 hours to form an at least partially deacetylated glycosaminoglycan; and
  a3) recovering the at least partially deacetylated glycosaminoglycan.

According to other aspects illustrated herein, there is provided a hydrogel product obtainable by the inventive method.

According to related aspects, the present disclosure also provides use of the hydrogel product as a medicament, such as in the treatment of soft tissue disorders. There is provided a method of treating a patient suffering from a soft tissue disorder by administering to the patient a therapeutically effective amount of the hydrogel product. There is also provided a method of providing corrective or aesthetic treatment to a patient by administering to the patient a therapeutically effective amount of the hydrogel product.

According to other aspects illustrated herein, there is provided a hydrogel product obtained by the inventive method for use as a medicament.

According to other aspects illustrated herein, there is provided a hydrogel product obtained by the inventive method for use in the treatment of soft tissue disorders.

According to other aspects illustrated herein, there is provided the use of a hydrogel product obtained by the inventive method for the manufacture of a medicament for treatment of soft tissue disorders.

According to other aspects illustrated herein, there is provided a method of treating a patient suffering from a soft tissue disorder by administering to the patient a therapeutically effective amount of a hydrogel product obtained by the inventive method.

According to other aspects illustrated herein, there is provided a method of providing corrective or aesthetic treatment to a patient by administering to the patient a therapeutically effective amount of a hydrogel product obtained by the inventive method.

According to other aspects illustrated herein, there is provided a method of cosmetically treating skin, which comprises administering to the skin a hydrogel product obtained by the inventive method.

Other aspects and preferred embodiments of the present invention will be evident from the following detailed disclosure of the invention and the appended claims.

DETAILED DESCRIPTION OF THE INVENTION

The present disclosure provides advantageous processes for preparing hydrogels made of crosslinked glycosaminoglycan (GAG) molecules, the resulting hydrogel products and uses thereof. GAGs are negatively charged heteropolysaccharide chains which have a capacity to absorb large amounts of water. In the hydrogel products according to the disclosure, the crosslinked GAG molecule is the swellable polymer which provides the gel properties. The preparation process described herein is mild to the GAG molecules but provides an efficient crosslinking.

The inventive method of preparing a hydrogel product comprising crosslinked glycosaminoglycan molecules, comprises:

i) providing a glycosaminoglycan crosslinked by amide bonds, wherein the crosslinked glycosaminoglycans comprise residual amine groups; and
ii) acylating residual amine groups of the crosslinked glycosaminoglycans provided in i) to form acylated crosslinked glycosaminoglycans.

According to some embodiments, i) comprises the steps:
a) providing a solution comprising an at least partially deacetylated glycosaminoglycan and optionally a second glycosaminoglycan;
b) activating carboxyl groups on the at least partially deacetylated glycosaminoglycan and/or the optional second glycosaminoglycan with a coupling agent, to form activated glycosaminoglycans;
c) crosslinking the activated glycosaminoglycans via their activated carboxyl groups using amino groups of the at least partially deacetylated glycosaminoglycans to provide glycosaminoglycans crosslinked by amide bonds.

The hydrogel products discussed herein are obtained by amide coupling of glycosaminoglycan molecules. Amide coupling using a using a di- or multiamine functional crosslinker together with a coupling agent is an attractive route to preparing crosslinked glycosaminoglycan molecules useful for hydrogel products. Amide crosslinking can be achieved using a non-carbohydrate based di- or multinucleofile crosslinker, for example hexamethylenediamine (NMDA), or a carbohydrate based di- or multinucleofile crosslinker, for example diaminotrehalose (DATH) together with a glycosaminoglycan. Crosslinking can also be achieved using an at least partially deacetylated glycosaminoglycan, either alone or in combination with a second glycosaminoglycan, whereby the deacetylated glycosaminoglycan itself acts as the di- or multinucleofile crosslinker.

Thus, the present disclosure provides GAG molecule hydrogels by crosslinking in aqueous media using a crosslinker comprising at least two nucleofile functional groups, for example amine groups, capable of forming covalent bonds directly with carboxylic acid groups of GAG molecules by a reaction involving the use of a coupling agent.

The crosslinker comprising at least two nucleofile functional groups may for example be a non-carbohydrate based di- or multinucleofile crosslinker or a carbohydrate based di- or multinucleofile crosslinker.

Carbohydrate based di- or multinucleofile crosslinkers are preferred, since they provide a hydrogel product based entirely on carbohydrate type structures or derivatives thereof. This could reduce the disturbance of the native properties of the glycosaminoglycans often caused by crosslinking with non-saccharide based crosslinkers. The crosslinker itself can also contribute to maintained or increased properties of the hydrogel, for example when crosslinking with a structure that correlates to hyaluronic acid or when crosslinking with a structure with high water retention properties.

The carbohydrate based di- or multinucleofile crosslinker may for example be selected from the group consisting of di- or multinucleofile functional di-, tri-, tetra-, oligosaccharides, and polysaccharides.

In a preferred embodiment, the di- or multinucleofile crosslinker is an at least partially deacetylated polysaccharide, i.e. an acetylated polysaccharide which has been at least partially deacetylated to provide a polysaccharide having free amine groups. An at least partially deacetylated glycosaminoglycan, can be crosslinked either alone or in combination with a second glycosaminoglycan, whereby the deacetylated glycosaminoglycan itself acts as the di- or multinucleofile crosslinker.

Figure 1:
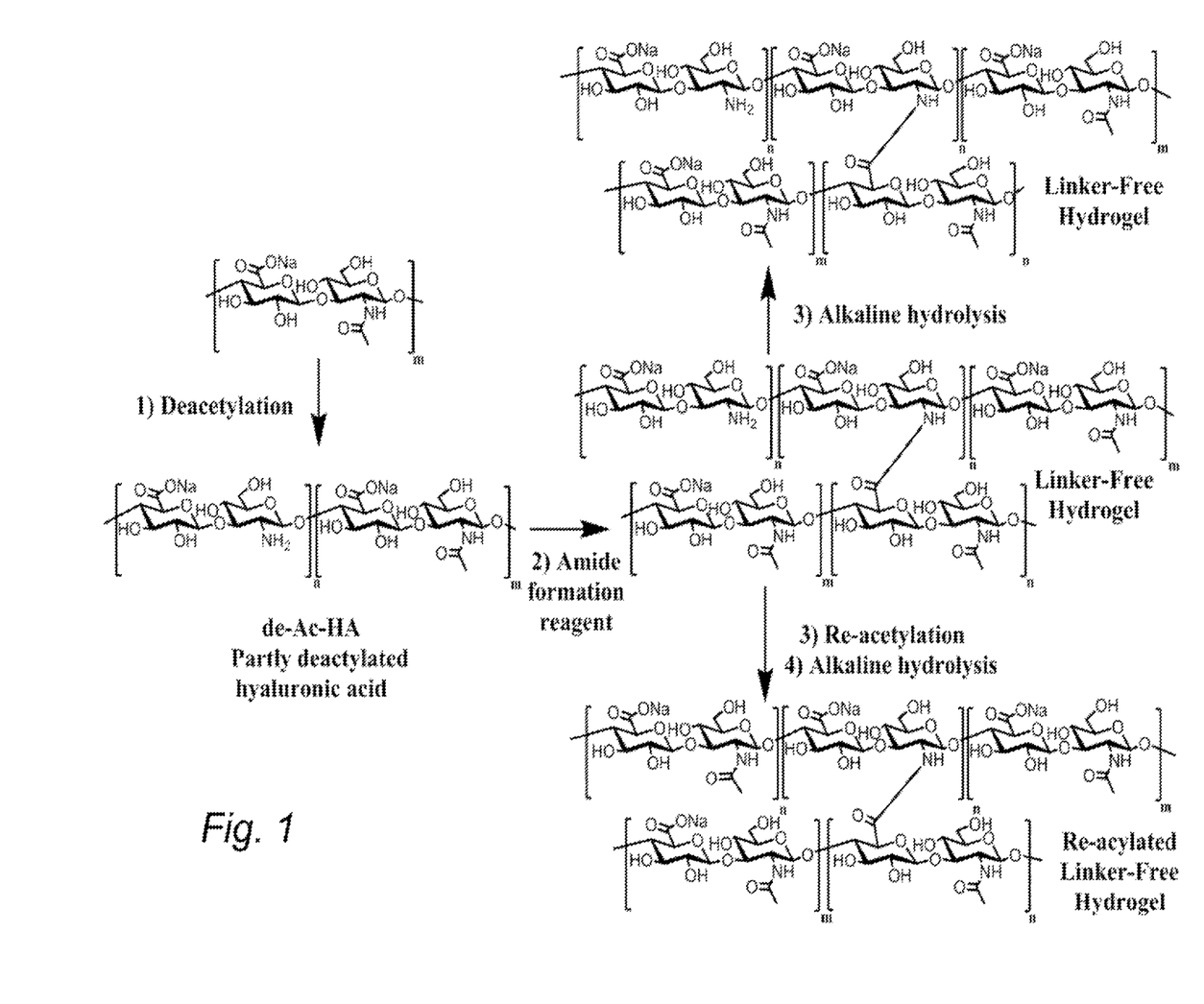
FIG. 1 is a reaction scheme illustrating the formation of a crosslinked hyaluronic acid comprising 1) deacetylation of hyaluronic acid to form partially deacetylated hyaluronic acid, 2) crosslinking the partially deacetylated hyaluronic by amide formation, and 3) re-acetylation of free amine groups and alkaline hydrolysis of ester bonds formed during the crosslinking and re-acetylation.
Figure 2:
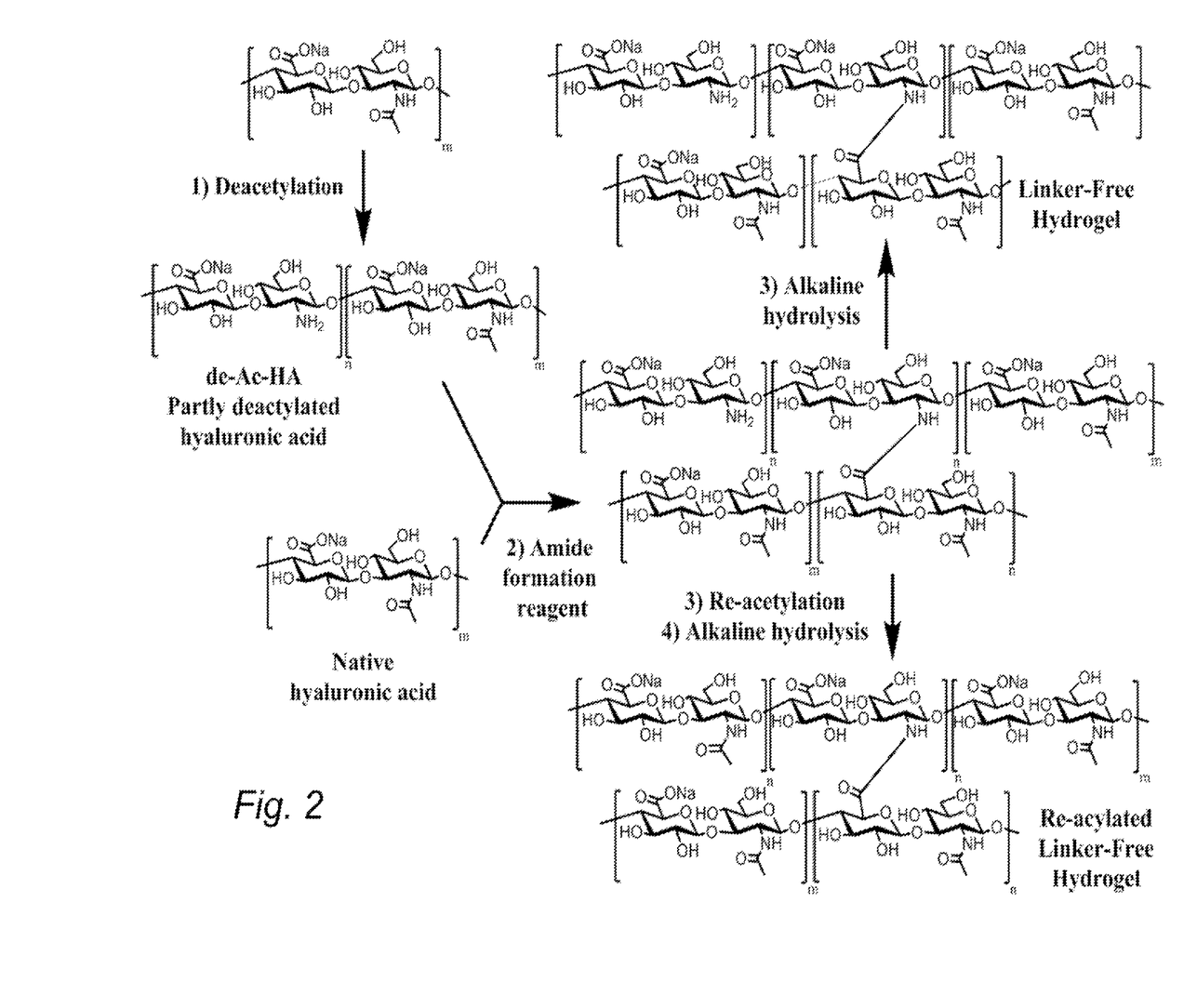
FIG. 2 is a reaction scheme illustrating the formation of a crosslinked hyaluronic acid comprising 1) deacetylation of hyaluronic acid to form partially deacetylated hyaluronic acid, 2) crosslinking the partially deacetylated hyaluronic to non-deacetylated hyaluronic acid by amide formation, and 3) re-acetylation of free amine groups and alkaline hydrolysis of ester bonds formed during the crosslinking and re-acetylation.

In a preferred embodiment, the crosslinked GAG is provided by:
1) crosslinking at least partially deacetylated GAG to partially deacetylated GAG using free amine and carboxylic acid groups present in the at least partially deacetylated GAGs, as shown in FIG. 1; or
2) crosslinking at least partially deacetylated GAG to a non-deacetylated GAG using free amine groups present in the at least partially deacetylated GAG and carboxylic acid groups present in the GAG, as shown in FIG. 2.

The GAG according to the present disclosure may for example be selected from the group consisting of sulfated or non-sulfated glycosaminoglycans such as hyaluronan, chondroitin, chondroitin sulphate, heparan sulphate, heparosan, heparin, dermatan sulphate and keratan sulphate. The GAG according to the present disclosure is preferably selected from the group consisting of hyaluronic acid, chondroitin and chondroitin sulfate. In a preferred embodiment, the GAG molecule is hyaluronic acid. Hyaluronic acid (HA) is one of the most widely used biocompatible polymers for medical and cosmetic use. HA is a naturally occurring polysaccharide belonging to the group of glycosaminoglycans (GAGs). Hyaluronic acid consists of two alternating monosaccharides units, D-N-acetyl glucosamine (GlcNAc) and D-glucuronic acid (GlcA), assembled by $\beta(1\rightarrow3)$ and $\beta(1\rightarrow4)$ glycosidic bonds, respectively. Hyaluronic acid and products derived from hyaluronic acid are widely used in the biomedical and cosmetic fields, for instance during viscosurgery and as a dermal filler.

Unless otherwise specified, the term "hyaluronic acid" encompasses all variants and combinations of variants of hyaluronic acid, hyaluronate or hyaluronan, of various chain lengths and charge states, as well as with various chemical modifications. That is, the term also encompasses the various hyaluronate salts of hyaluronic acid with various counter ions, such as sodium hyaluronate. The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

The term "chondroitin" refers to GAGs having a disaccharide repeating unit consisting of alternating non-sulfated D-glucuronic acid and N-acetyl-D-galactosamine moieties. For avoidance of doubt, the term "chondroitin" does not encompass any form of chondroitin sulfate.

The term "chondroitin sulfate" refers to GAGs having a disaccharide repeating unit consisting of alternating D-glucuronic acid and N-acetyl-D-galactosamine moieties. The sulfate moiety can be present in various different positions. Preferred chondroitin sulfate molecules are chondroitin-4-sulfate and chondroitin-6-sulfate.

The chondroitin molecules can be obtained from various sources of animal and non-animal origin. Sources of non-animal origin include yeast and preferably bacteria. The molecular weight of a single chondroitin molecule is typically in the range of 1-500 kDa, but other molecular weights are possible.

According to some embodiments, the at least partially deacetylated glycosaminoglycan employed in step a) of the method of preparing a hydrogel product is a deacetylated glycosaminoglycan having a degree of acetylation of 99% or less, preferably 98% or less, preferably 97% or less, preferably 96% or less, preferably 95% or less, preferably 94% or less, preferably 93% or less, and a weight average molecular weight of 0.1 MDa or more, preferably 0.5 MDa or more. According to some embodiments, the at least partially deacetylated glycosaminoglycan employed in step a) of the method of preparing a hydrogel product is obtained by the deacetylation methods described above.

According to some embodiments, the at least partially deacetylated glycosaminoglycan employed in step a) of the method of preparing a hydrogel product is a deacetylated glycosaminoglycan selected from the group consisting of deacetylated sulfated or non-sulfated glycosaminoglycans such as deacetylated hyaluronan, deacetylated chondroitin, deacetylated chondroitin sulphate, deacetylated heparan sulphate, deacetylated heparosan, deacetylated heparin, deacetylated dermatan sulphate and deacetylated keratan sulphate. Preferably, the at least partially deacetylated glycosaminoglycan employed in step a) of the method of preparing a hydrogel product is selected from the group consisting of deacetylated hyaluronic acid, deacetylated chondroitin and deacetylated chondroitin sulfate, and mixtures thereof. Preferably, the at least partially deacetylated glycosaminoglycan employed in step a) of the method of preparing a hydrogel product is deacetylated hyaluronic acid.

According to some embodiments, the optional second glycosaminoglycan employed in step a) of the method of preparing a hydrogel product is a glycosaminoglycan selected from the group consisting of sulfated or non-sulfated glycosaminoglycans such as hyaluronan, chondroitin, chondroitin sulphate, heparan sulphate, heparosan, heparin, dermatan sulphate and keratan sulphate. Preferably, the optional second glycosaminoglycan employed in step a) of the method of preparing a hydrogel product is selected from the group consisting of hyaluronic acid, chondroitin and chondroitin sulfate, and mixtures thereof. Preferably, the optional second glycosaminoglycan employed in step a) of the method of preparing a hydrogel product is hyaluronic acid.

Crosslinking glycosaminoglycans directly via formation of amide bonds between amino and carboxyl groups present on the glycosaminoglycans provides a hydrogel product based entirely on carbohydrate type structures.

The method of preparing a hydrogel product involves crosslinking of glycosaminoglycan molecules by covalent bonds, preferably amide bonds, typically using an activating agent for the carboxyl groups on the glycosaminoglycan molecule backbone and amino groups of an at least partially deacetylated glycosaminoglycan. Crosslinking according to the inventive method can be achieved by mild and efficient routes resulting in high yields with minimal degradation of the glycosaminoglycan molecules.

According to some embodiments, the activation step b) and the crosslinking step c) occur simultaneously.

According to some embodiments, the coupling agent of step b) is a peptide coupling reagent. Crosslinking using a peptide coupling agent is advantageous over many other common crosslinking methods (e.g. BDDE crosslinking) since it allows for crosslinking to be performed at neutral pH with minimal degradation of the glycosaminoglycan molecules.

According to some embodiments, the peptide coupling reagent is selected from the group consisting of triazine-based coupling reagents, carbodiimide coupling reagents, imidazolium-derived coupling reagents, Oxyma and COMU.

According to some embodiments, the peptide coupling reagent is a triazine-based coupling reagent. According to some embodiments, the triazine-based coupling reagent is selected from the group consisting of 4-(4,6-dimethoxy-1, 3,5-triazin-2-yl)-4-methylmorpholinium chloride (DMTMM) and 2-chloro-4,6-dimethoxy-1,3,5-triazine (CDMT). According to some embodiments, the triazine-based coupling reagent is DMTMM.

According to some embodiments, the peptide coupling reagent is a carbodiimide coupling reagent. According to some embodiments, the carbodiimide coupling reagent is N-(3-dimethylaminopropyl)-N'-ethylcarbodiimide (EDC) combined with N-hydroxysuccinimide (NHS).

Another preferred peptide coupling reagent is 2-chloro-1-methylpyridinium iodide (CMPI).

The term "crosslinked glycosaminoglycans" or "crosslinked glycosaminoglycan molecules" refers herein to glycosaminoglycans comprising, typically covalent, crosslinks between the glycosaminoglycan molecule chains, which creates a continuous network of glycosaminoglycan molecules held together by the crosslinks.

The crosslinked GAG product is preferably biocompatible. This implies that no, or only very mild, immune response occurs in the treated individual. That is, no or only very mild undesirable local or systemic effects occur in the treated individual.

The crosslinked product according to the disclosure is a gel, or a hydrogel. That is, it can be regarded as a water-insoluble, but substantially dilute crosslinked system of GAG molecules when subjected to a liquid, typically an aqueous liquid.

The crosslinked GAG molecule is preferably present in the form of gel particles. The gel particles preferably have an average size in the range of 0.01-5 mm, preferably 0.1-0.8 mm, such as 0.2-0.5 mm or 0.5-0.8 mm.

According to some embodiments, the method further comprises providing particles of the crosslinked glycosaminoglycans, having an average size in the range of 0.01-5 mm, preferably 0.1-0.8 mm, such as 0.2-0.5 mm or 0.5-0.8 mm.

The gel contains mostly liquid by weight and can e.g. contain 90-99.9%, water, but it behaves like a solid due to a three-dimensional crosslinked GAG molecule network within the liquid. Due to its significant liquid content, the gel is structurally flexible and similar to natural tissue, which makes it very useful as a scaffold in tissue engineering and for tissue augmentation. It is also useful for treatment of soft tissue disorder and for corrective or aesthetic treatment. It is preferably used as an injectable formulation.

The hydrogel product may also comprise a portion of GAG molecules which are not crosslinked, i.e not bound to the three-dimensional crosslinked GAG molecule network. However, it is preferred that at least 50% by weight, preferably at least 60% by weight, more preferably at least 70% by weight, and most preferably at least 80% by weight, of the GAG molecules in a gel composition form part of the crosslinked GAG molecule network.

The hydrogel product may be present in an aqueous solution, but it may also be present in dried or precipitated form, e.g. in ethanol. The hydrogel product is preferably injectable.

According to some embodiments, the at least partially deacetylated glycosaminoglycan is obtained by a method for at least partial deacetylation of a biopolymer, wherein the biopolymer is a glycosaminoglycan, the method comprising:
  a1) providing a biopolymer comprising acetyl groups;
  a2) reacting the biopolymer comprising acetyl groups with hydroxylamine ($NH_2OH$) or a salt thereof at a temperature of 100° C. or less for 2-200 hours to form an at least partially deacetylated biopolymer; and a3) recovering the at least partially deacetylated biopolymer.

The term "biopolymer" as used herein refers to polymers produced by living organisms. Biopolymers are divided into the three main classes, polynucleotides, polypeptides and polysaccharides.

It has been found that hydroxylamine ($NH_2OH$) and salts thereof can advantageously be used for deacetylation of biopolymer comprising acetyl groups under mild reaction conditions. The deacetylated biopolymers may be useful for various applications, e.g. for crosslinking, conjugation or grafting reactions, requiring the presence of free amine groups.

The inventive deacetylation method involves a hydroxylaminolysis reaction. Using hydroxylamine or a salt thereof for deacetylation has been found to allow for N-deacetylation under mild conditions resulting in only minor degradation of the polymeric backbone of sensitive polysaccharides such as HA. Using hydroxylamine or a salt thereof for deacetylation thus allows for production of deacetylated HA with retained high molecular weight. This is in contrast to previously known methods, such as deacetylation using hydrazine or NaOH as the deacetylating agent, where high degrees of deacetylation have been inevitably accompanied by severe degradation of the polymeric backbone.

The step of recovering the at least partially deacetylated biopolymer may involve simply keeping or using the deacetylated biopolymer as it is obtained. The step of recovering the at least partially deacetylated biopolymer may also involve any further treatment of the deacetylated biopolymer, including but not limited to washing and purification.

The biopolymer comprising acetyl groups is a glycosaminoglycan, preferably selected from the group consisting of hyaluronic acid, chondroitin and chondroitin sulfate, and mixtures thereof. According to some embodiments, the biopolymer comprising acetyl groups is hyaluronic acid.

Polysaccharides, and particularly glycosaminoglycans such as hyaluronic acid, chondroitin and chondroitin sulfate, are often prone to degradation of the backbone under harsh reaction conditions (e.g. very high or low pH, or high temperatures). The inventive method is therefore especially useful for deacetylation of such polysaccharides.

The inventive deacetylation method is useful for obtaining at least partially deacetylated biopolymers in which a significant portion of the molecular weight of the starting material is retained.

According to some embodiments, the weight average molecular weight of the recovered at least partially deacetylated biopolymer is at least 10%, preferably at least 20%, more preferably at least 25%, of the weight average molecular weight of the biopolymer comprising acetyl groups in step a1). The weight average molecular weight of the recovered at least partially deacetylated biopolymer may also be higher, such as at least 30%, 40%, 50%, 60%, 70%, 80% or 90% of the weight average molecular weight of the biopolymer comprising acetyl groups in step a1).

According to some embodiments, the biopolymer comprising acetyl groups used as the starting material in the deacetylation method has a weight average molecular weight of at least 10 kDa. According to some embodiments, the biopolymer comprising acetyl groups has a weight average molecular weight of at least 100 kDa, of at least 500 kDa, of at least 750 kDa, or of at least 1 MDa. According to some embodiments, the biopolymer comprising acetyl groups has a weight average molecular weight in the range of 1-5 MDa, preferably in the range of 2-4 MDa.

According to some embodiments, the recovered at least partially deacetylated biopolymer has a weight average molecular weight of at least 10 kDa.

According to some embodiments, the recovered at least partially deacetylated biopolymer has a weight average molecular weight of at least 100 kDa, of at least 500 kDa, of at least 750 kDa, or of at least 1 MDa. According to some embodiments, the recovered at least partially deacetylated biopolymer has a weight average molecular weight in the range of 0.1-5 MDa, preferably in the range of 0.5-5 MDa or 0.5-3 MDa.

The deacetylation method of the present disclosure is also applicable to shorter biopolymers, or biooligomers, such as dimers, trimers, tetramers, etc.

According to some embodiments, the biopolymer comprising acetyl groups used as the starting material in the deacetylation method is an oligobiopolymer which has a weight average molecular weight in the range of 0.3-10 kDa.

According to some embodiments, the recovered at least partially deacetylated oligobiopolymer has a weight average molecular weight in the range of 0.3-10 kDa.

The biopolymer comprising acetyl groups used as the starting material in the deacetylation method is typically fully, or almost fully, acetylated. By the term "fully acetylated" as used herein with reference to the biopolymer, we mean a biopolymer in which all, or substantially all, free amine groups have been converted to N-acetyl groups. In other words, the "fully acetylated" biopolymer comprises no, or substantially no, free amine groups. According to some embodiments, the biopolymer comprising acetyl groups used as the starting material in step a1) has a degree of acetylation in the range of 98-100%.

According to some embodiments, the recovered at least partially deacetylated biopolymer has a degree of acetylation at least 1% less, preferably at least 2% less, preferably at least 3% less, preferably at least 4% less, preferably at least 5% less, than that of the biopolymer comprising acetyl groups in step a1). In other words, the recovered at least partially deacetylated biopolymer may have a degree of acetylation of less than 99%, preferably less than 98%, less than 97%, less than 97%, less than 96%, less than 95%, less than 94% or less than 93%. The recovered at least partially deacetylated biopolymer may also have a degree of acetylation at least 10% less, at least 15% less, at least 20% less, at least 30% less, at least 40% less, or at least 50%, less than that of the biopolymer comprising acetyl groups in step a1). In a preferred embodiment, the at least partially deacetylated biopolymer has a degree of acetylation of less than 97%.

The deacetylation can be achieved using hydroxylamine or salt thereof. The hydroxylamine salt refers to a salt formed by hydroxylamine and an acid. The hydroxylamine salt may for example be a salt formed by hydroxylamine and an acid selected from the group consisting of mineral acids and organic acids or mixtures thereof.

According to embodiments, the hydroxylamine salt is a salt formed by hydroxylamine and a mineral acid. According to embodiments, the acid is selected from the group consisting of sulfuric acid, hydrochloric acid, hydroiodic acid, hydrobromic acid and phosphoric acid, and combinations thereof. Preferred mineral acids include hydrochloric acid, hydroiodic acid and hydrobromic acid. A particularly preferred mineral acid is hydroiodic acid.

According to embodiments, the hydroxylamine salt is a salt formed by hydroxylamine and an organic acid. According to embodiments, the acid is selected from the group consisting of acetic acid, propionic acid, pivalic acid, citric acid, oxalic acid, malonic acid, lactic acid, benzoic acid, and halogenated carboxylic acids, such as trifluoroacetic acid (TFA) and trichloroacetic acid, and combinations thereof.

According to embodiments, the acid is selected from the group consisting of acetic acid, propionic acid, pivalic acid, and a halogenated carboxylic acid, preferably trifluoroacetic acid, and combinations thereof. According to embodiments, the acid is a halogenated carboxylic acid, preferably trifluoroacetic acid.

According to embodiments, the hydroxylamine salt is a salt formed by hydroxylamine and an acid selected from the group consisting of hydrochloric acid, hydroiodic acid and hydrobromic acid, propionic acid, pivalic acid and trifluoroacetic acid.

The reaction in step a2 is preferably performed in a solvent capable of at least partially dissolving both the biopolymer comprising acetyl groups and the hydroxylamine or salt thereof. The solvent may for example be water or an organic solvent or a mixture thereof. Non-limiting examples of preferred solvents include water or a mixture of water and a lower alcohol, such as ethanol. However, may other solvents would be useful, depending on the particular biopolymer, and the selection of hydroxylamine or salt thereof. One example of a useful organic solvent is tetrahydrofuran (THF).

According to embodiments, the reaction in step a2) comprises reacting the molecule comprising an amide group with hydroxylamine in water.

The deacetylation process may preferably be performed in water or aqueous solution, optionally further comprising another solvent, such as ethanol. Thus according to some embodiments, step a1) comprises contacting a biopolymer comprising acetyl groups with hydroxylamine in water so that an aqueous mixture or solution of the biopolymer and the hydroxylamine is formed. In some embodiments, the concentration of hydroxylamine is at least 10% by weight, preferably at least 20% by weight, preferably at least 30% by weight of the aqueous mixture or solution. A higher concentration of hydroxylamine may increase the reaction rate.

Hydroxylamine is often provided in the form of an aqueous solution, typically at a concentration of 50% by weight. In some embodiments, the biopolymer may be mixed and dissolved directly in the aqueous solution of hydroxylamine, optionally diluted. Alternatively, a solid salt of hydroxylamine, for example hydroxylamine hydrochloride or hydroxylamine sulfate, can be dissolved in an aqueous solution of the biopolymer. Adding a salt of hydroxylamine, and converting the salt to hydroxylamine, may be done as an alternative or as a complement to dissolving the biopolymer comprising acetyl groups in an aqueous solution of hydroxylamine.

The molar concentration of hydroxylamine in the reaction mixture is preferably in the range of 5-20 M. For example, a concentration of hydroxylamine of 50% by weight roughly corresponds to a molar concentration of 16 M.

The inventors have surprisingly found that when a hydroxylamine salt is used instead of hydroxylamine itself, the same reaction rate can be achieved with a significantly lower molar concentration. Thus, the molar concentration of hydroxylamine salt in the reaction mixture is preferably in the range of 0.01-10 M, preferably in the range of 0.1-5 M.

According to some embodiments, the biopolymer comprising acetyl groups is dissolved in an aqueous solution of hydroxylamine or a salt thereof in step a1). According to some embodiments, a salt of hydroxylamine is dissolved in an aqueous solution of a biopolymer comprising acetyl groups in step a1). According to some embodiments, the biopolymer comprising acetyl groups is dissolved in an aqueous solution of hydroxylamine, and a salt of hydroxylamine is dissolved in the aqueous solution of biopolymer comprising acetyl groups in hydroxylamine.

The inventors have surprisingly found that when a hydroxylamine salt is used instead of hydroxylamine itself, the same reaction rate can be achieved with a significantly lower molar concentration. Thus, the molar concentration of hydroxylamine salt in the reaction mixture is preferably in the range of 0.01-10 M, preferably in the range of 0.1-5 M.

According to some embodiments, the biopolymer comprising acetyl groups is dissolved in an aqueous solution of hydroxylamine or a salt thereof in step a1). According to some embodiments, a salt of hydroxylamine is dissolved in an aqueous solution of a biopolymer comprising acetyl groups in step a1). According to some embodiments, the biopolymer comprising acetyl groups is dissolved in an aqueous solution of hydroxylamine, and a salt of hydroxylamine is dissolved in the aqueous solution of biopolymer comprising acetyl groups in hydroxylamine.

The reaction temperature in step a2) is preferably 100° C. or less. The reaction temperature in step a2) is selected so as not to cause excessive degradation of the biopolymer. According to some embodiments, the temperature in step a2) is in the range of 10-90° C., preferably 20-80° C., preferably 30-70° C., preferably 30-50° C. According to embodiments, the reaction in step a2) comprises reacting the molecule comprising an amide group with the hydroxylamine or salt thereof at a temperature in the range of 10-100° C., preferably 20-90° C., preferably 30-70° C., preferably 30-50° C. The temperature may for example be in the range of 70-90° C., such as about 80° C., or in the range of 30-50° C., such as about 40° C.

The reaction time in step a2) depends on the desired degree of deacetylation. The reaction time is preferably selected so as not to cause excessive degradation of the biopolymer and is also dependent on the temperature and pH. The reaction time may generally be anywhere from 5 minutes to 200 hours or more. According to some embodiments, the reaction in step a2) comprises reacting the molecule comprising an amide group with the hydroxylamine or salt thereof for 2-200 hours. According to some embodiments, the reaction in step a2) comprises reacting the molecule comprising an amide group with the hydroxylamine or salt thereof for 2-150 hours, preferably 5-150 hours, preferably 5-100 hours. In other embodiments, e.g. where a higher temperature or pH is used, the reaction time can be much shorter, such as in the range of 5 minutes to 2 hours, in the range of 30 minutes to 2 hours, or in the range of 1-2 hours.

The pH in step a2) is preferably selected so as not to cause excessive degradation of the biopolymer. According to some embodiments, the reaction in step a2) is performed at a pH value in the range of 4-12. According to some embodiments, the reaction in step a2) is performed at a pH value in the range of 9-11. According to some embodiments, the reaction in step a2) is performed at a pH value in the range of 4-9, preferably in the range of 6-9, preferably in the range of 6-8 or 7-8. A lower pH (e.g. about neutral pH), such as in the range of 6-8 or 7-8, is typically preferred in order to avoid degradation of the biopolymer.

The inventors have found through extensive experimentation that addition of a pH reducing agent can also significantly increase the reaction rate of the reaction in step a2), particularly when hydroxylamine is used. This effect is both surprising and highly advantageous. It is noted that a corresponding addition of a pH reducing agent to a hydrazine deacetylation reaction did not result in any increase of the reaction rate. A lower pH value during the reaction is also preferred in order to avoid excessive degradation of the biopolymer. Thus, according to some embodiments, the pH of the reaction is lowered to a value in the range of 4-9, preferably in the range of 6-9, preferably in the range of 6-8 or 7-8, by addition of a pH reducing agent. The pH reducing agent may for example be selected from the group consisting of mineral acids, organic acids and pH reducing salts, and mixtures or combinations thereof. Examples of useful mineral acids include, but are not limited to, sulfuric acid, hydrochloric acid and hydroiodic acid, hydrobromic acid and phosphoric acid. Examples of useful organic acids include, but are not limited to, acetic acid, propionic acid, pivalic acid, citric acid, oxalic acid, malonic acid, lactic acid, benzoic acid, and halogenated carboxylic acids, such as trifluoroacetic acid and trichloroacetic acid. Examples of useful pH reducing salts include, but are not limited to, ammonium chloride, ammonium bromide, ammonium iodide, hydroxylamine hydrochloride and hydroxylamine sulfate. In a preferred embodiment, the pH reducing agent comprises hydroxylamine hydrochloride or hydroxylamine sulfate, most preferably hydroxylamine hydrochloride. In some embodiments, the pH reducing agent is hydroiodic acid (HI). In some embodiments, the pH reducing agent is trifluoroacetic acid (TFA).

According to some embodiments, the reaction in step a2) is performed in inert atmosphere and/or in darkness.

The products obtained by the deacetylation method described above may have properties that differ significantly from corresponding products obtained by other known deacetylation methods.

The hydrogel product provided by the inventive method is subjected to the step ii) of acylating residual amine groups of the crosslinked glycosaminoglycans provided in step i) to form acylated crosslinked glycosaminoglycans. This process is also referred to herein as re-acylation, or re-acetylation.

It has been found that acylation, for example acetylation, of residual free amine groups in a hydrogel product comprising amide crosslinked glycosaminoglycan molecules can be used to modify the mechanical properties of the hydrogel product. Without wishing to be bound to any specific scientific explanation, it is contemplated that acylation of the free amine groups can reduce the formation of zwitterionic complexes acting as additional crosslinks in the hydrogel product, thereby resulting in the formation of a softer gel.

According to some embodiments, the step ii) comprises acetylating residual amine groups of the crosslinked glycosaminoglycans provided in step i) to form acetylated crosslinked glycosaminoglycans. Glycosaminoglycans in their native form are N-acetylated. Acetylation of free amine groups in a hydrogel product may therefore be expected to produce a hydrogel product more similar to the native glycosaminoglycans.

According to some embodiments, the step ii) comprises allowing the crosslinked glycosaminoglycans provided in step i) to react with an acetylating agent under reaction conditions suitable to form acetylated crosslinked glycosaminoglycans.

According to some embodiments, the acetylating agent is selected from the group consisting of acetic anhydride, isopropenyl acetate and pre-activated ester of acetic acid.

The re-acetylation can be performed according to standard protocol using e.g. acetic anhydride, isopropenyl acetate or pre-activated ester of acetic acid, typically in aqueous or alcoholic solution, or mixtures thereof, or under neat conditions. Preferably the re-acetylation process can be performed in a solid state reaction using alcohol, preferably methanol or ethanol, an acetylating agent and, if desired, an organic or inorganic base.

The potential problem of over-acetylation (O-acetylation), ester formation and/or anhydride formation, can be dealt with by including an optional post-crosslinking alkaline treatment step.

The hydrogel product obtained by the inventive method is optionally subjected to the step iii) of subjecting the crosslinked glycosaminoglycans provided in step i) or ii) to alkaline treatment to hydrolyze ester crosslinks formed as byproducts during the amide crosslinking.

Amide coupling using a using a di- or multiamine functional crosslinker together with a coupling agent is an attractive route to preparing crosslinked glycosaminoglycan molecules useful for hydrogel products. Crosslinking can be achieved using a non-carbohydrate based di- or multinucleofile crosslinker, for example hexamethylenediamine (NMDA), or a carbohydrate based di- or multinucleofile crosslinker, for example diaminotrehalose (DATH) together with a glycosaminoglycan. Crosslinking can also be achieved using an at least partially deacetylated glycosaminoglycan, either alone or in combination with a second glycosaminoglycan, whereby the deacetylated glycosaminoglycan itself acts as the di- or multinucleofile crosslinker.

It has been found that coupling reactions or crosslinking of glycosaminoglycans using coupling agents to form amide bonds are often associated with the concurrent formation of a fraction of ester bonds. The size of the ester bond fraction may vary depending on the reaction conditions, concentrations and coupling agent used. Ester bonds are more susceptible to degradation during handling and storage of the hydrogel products, for example high temperature sterilization (autoclaving), compared to amide bonds. This means that the properties of hydrogel products comprising ester bonds, or a combination of ester and amide bonds, will tend to change over time as the ester bonds degrade. In order to obtain hydrogels which maintain their original properties over a longer period of time, and it is preferable that the glycosaminoglycans are crosslinked by amide bonds.

The present inventors have now found that subjecting the crosslinked glycosaminoglycans having both amide and ester crosslinks to alkaline treatment can hydrolyze ester crosslinks formed as byproducts during the amide crosslinking without concurrently degrading the amide bonds. It has further been found that upon selection of suitable reaction conditions the hydrolysis of the ester bonds can be achieved without undue degradation of the glycosaminoglycan backbone.

The method of preparing a hydrogel product optionally comprises the step ii) of acylating residual amine groups of the crosslinked glycosaminoglycans provided in step i) to form acylated crosslinked glycosaminoglycans Acylation, for example acetylation, of residual free amine groups in a hydrogel product comprising amide crosslinked glycosaminoglycan molecules can be used to modify the mechanical properties of the hydrogel product. Without wishing to be bound to any specific scientific explanation, it is contemplated that acylation of the free amine groups can reduce the formation of zwitterionic complexes acting as additional crosslinks in the hydrogel product, thereby resulting in the formation of a softer gel.

According to some embodiments, the step ii) comprises acetylating residual amine groups of the crosslinked glycosaminoglycans provided in step i) to form acetylated crosslinked glycosaminoglycans. Glycosaminoglycans in their native form are N-acetylated. Acetylation of free amine groups in a hydrogel product may therefore be expected to produce a hydrogel product more similar to the native glycosaminoglycans.

Acylation of glycosaminoglycans using an acylating agent to form amide bonds is often associated with the concurrent formation of a fraction of ester bonds. The size of the ester bond fraction may vary depending on the reaction conditions, concentrations and the acylating agent used. Ester bonds are more susceptible to degradation during handling and storage of the hydrogel products, for example high temperature sterilization (autoclaving), compared to amide bonds. This means that the properties of hydrogel products comprising ester bonds, or a combination of ester and amide bonds, will tend to change over time as the ester bonds degrade. In order to obtain hydrogels which maintain their original properties over a longer period of time, and it is preferable that the glycosaminoglycans are acylated by amide bonds.

The present inventors have now found that subjecting the acylated crosslinked glycosaminoglycans having both amide and ester crosslinks to alkaline treatment can hydrolyze ester bonds formed during the acylation without concurrently degrading the amide bonds. It has further been found that upon selection of suitable reaction conditions the hydrolysis of the ester bonds can be achieved without undue degradation of the glycosaminoglycan backbone.

The alkaline treatment selectively hydrolyses the less stable ester bonds from the crosslinking process, or O-acetylation and anhydride formation from the re-acetylation process, and results in an increased amide/ester bond ratio in the material.

A typical application of the resulting hydrogel product involves the preparation of injectable formulations for treatment of soft tissue disorders, including, but not limited to, corrective and aesthetic treatments.

The term "molecular weight" as used herein in connection with various polymers, e.g. polysaccharides, refers to the weight average molecular weight, Mw, of the polymers, which is well defined in the scientific literature.

The weight average molecular weight can be determined by, e.g., static light scattering, small angle neutron scattering, X-ray scattering, and sedimentation velocity. The unit of the molecular weight is Da or g/mol.

The person skilled in the art realizes that the present invention by no means is limited to the preferred embodiments described herein. On the contrary, many modifications and variations are possible within the scope of the appended claims. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

EXAMPLES

Without desiring to be limited thereto, the present invention will in the following be illustrated by way of examples.

Definitions and Analysis

Mw—The mass average molecular mass
SwF—Swelling factor analysis in saline, volume for a 1 g gel that has swelled to its maximum (mL/g)
SwC—Swelling capacity in saline, total liquid uptake per gram PS (mL/g).
$SwCC_{PS}$—Corrected swelling degree, total liquid uptake of one gram PS, corrected for GelP (mL/g).

$$SwCC_{PS} = \frac{SwF}{GelP * [HA]}$$

[PS]—The polysaccharide concentration (mg/g).
GelP—Gel part is a description of the percentage of PS that is a part of the gel network. A number of 90% means that 10% of the polysaccharide is not a part of the gel network.
$CrD_{amide}$—Degree of amide cross-linking (%) was analyzed with SEC-MS and defined as:

$$CrD_{amide} = \frac{n_{amide\ crosslinks}}{n_{HA\ disaccharides}}$$

$$CrD_{amide} = \frac{\sum(\text{Area amide crosslinked } HA \text{ fragments})}{\sum(\text{Area amide crosslinked } HA \text{ fragments}+ \text{Area } HA \text{ amine fragments})} * (100 - DoA)$$

DoA—Degree of Acetylation. The degree of acetylation (DoA) is the molar ratio of acetyl groups compared to hyaluronic acid disaccharides. DoA can be calculated from NMR spectra by comparing the integral of the acetyl signal of the hyaluronan disaccharide residues to the integral of the C2-H signal of the deacetylated glucosamine residues according to the equation.

$$DoA\ (\%) = \left( \frac{\frac{\text{Integral } acetylgroup}{3}}{\frac{\text{Integral } acetylgroup}{3} + \text{Integral } C2-H} \right) * 100$$

NMR—$^1$H NMR spectra were recorded on a BRUKER Biospin AVANCE 400 spectrometer. Chemical shifts are reported as δ values downfield from internal TMS in appropriate organic solutions. The purity and the structures of the products were confirmed by LCMS (254 nm) on a Waters 2690 photodiode array detector system using the following conditions: Column, Symmetry C-18; Solvent A, water 0.1% formic acid; Solvent B, $CH_3CN$; flow rate, 2.5 ml/min; run time, 4.5 min; gradient, from 0 to 100% solvent B; mass detector, micro mass ZMD. Purifications were carried out directly by mass-triggered preparative LCMS Waters X-Terra reverse-phase column (C-18, 5 microns silica, 19 mm diameter, 100 mm length, flow rate of 40 ml/minute) and decreasingly polar mixtures of water (containing 0.1% formic acid) and acetonitrile as eluent. The fractions containing the desired compound were evaporated to dryness to afford the final compounds usually as solids.

Example 1—Deacetylation of Hyaluronic Acid by Hydroxylaminolysis 0.2 g or 20 g of HA (Mw 2 500 kDa, DoA 100%) was solubilised in hydroxylamine (Sigma-Aldrich 50 vol % solution), or a mixture of hydroxylamine/water as set out in Table 1. The solution was incubated in darkness and under argon at 30-70° C. for 5-353 hours. After incubation, the mixture was precipitated by ethanol. The obtained precipitate was filtered, washed with ethanol and then re-dissolved in water. The solution was purified by ultrafiltration and subsequently lyophilized to obtain the deacetylated HA (de-Ac HA) as a white solid. Examples 1-1 to 1-14 were performed using approx. 0.2 g HA and examples 1-15 to 1-16 were performed using 20 g HA. Deacetylation by hydroxylaminolysis is more efficient, and conserves the Mw of the HA backbone better as compared to hydrazinolysis (example 2) and alkaline methods (example 3 and 4).

TABLE 1

| Example | Temp (° C.) | Time (h) | pH | Conditions | Start Mw (kDa) | NMR DoA (%) | Mw (kDa) |
|---|---|---|---|---|---|---|---|
| 1-1 | 30 | 24 | 10 | NH$_2$OH (50 wt. % in water) | 2500 | 99 | 970 [a] |
| 1-2 | 30 | 72 | 10 | NH$_2$OH (50 wt. % in water) | 2500 | 98 | 1060 [a] |
| 1-3 | 30 | 196 | 10 | NH$_2$OH (50 wt. % in water) | 2500 | 95 | 1060 [a] |
| 1-4 | 40 | 24 | 10 | NH$_2$OH (50 wt. % in water) | 2500 | 98 | 1050 [a] |
| 1-5 | 40 | 72 | 10 | NH$_2$OH (50 wt. % in water) | 2500 | 95 | 980 [a] |
| 1-6 | 40 | 353 | 10 | NH$_2$OH (50 wt. % in water) | 2500 | 80 | 490 [a] |
| 1-7 | 40 | 24 | 10 | NH$_2$OH (35 wt. % in water) | 2500 | 99 | 1090 [a] |
| 1-8 | 40 | 24 | 10 | NH$_2$OH (20 wt. % in water) | 2500 | 100 | 1130 [a] |
| 1-9 | 40 | 24 | 10 | NH$_2$OH (50 wt. % in water) | 1000 | 98 | 670 [b] |
| 1-10 | 55 | 5 | 10 | NH$_2$OH (50 wt. % in water) | 2500 | 99 | 1010 [a] |
| 1-11 | 55 | 72 | 10 | NH$_2$OH (50 wt. % in water) | 2500 | 86 | 740 [a] |
| 1-12 | 55 | 120 | 10 | NH$_2$OH (50 wt. % in water) | 2500 | 78 | 400 [b] |
| 1-13 | 60 | 24 | 10 | NH$_2$OH (50 wt. % in water) | 2500 | 92 | 930 [b] |
| 1-14 | 70 | 24 | 10 | NH$_2$OH (50 wt. % in water) | 2500 | 86 | 720 [b] |
| 1-15 | 40 | 72 | 10 | NH$_2$OH (50 wt. % in water) | 2500 | 95 | 1870 [b] |
| 1-16 | 55 | 72 | 10 | NH$_2$OH (50 wt. % in water) | 2500 | 89 | 1050 [b] |

[a] SEC-UV
[b] SEC-MALS

Example 2—Deacetylation of Hyaluronic Acid by Hydrazinolysis—Comparative Example 0.2 g of HA (Mw 2 500 kDa, DoA 100%) was solubilised in 10 mL of a 1% solution of hydrazine sulphate in hydrazine monohydrate as set out in Table 2. The reaction took place in dark and under argon at 30-55° C. for 24-120 hours. The mixture was precipitated by ethanol. The precipitate obtained was filtered, washed with ethanol and then re-dissolved in water. The final deacetylated HA product was obtained after ultrafiltration, and freeze-dried. Deacetylation by hydrazinolysis gives more degradation of the HA backbone, i.e. lower Mw of the deacetylated product as compared to hydroxylaminolysis (Example 1).

TABLE 2

| Example | Temp (° C.) | Time (h) | pH | Conditions | DoA (%) | Mw (SEC MALS) (kDa) |
|---|---|---|---|---|---|---|
| 2-1 | 30 | 24 | 13 | NH$_2$NH$_2$ + NH$_2$NH$_2$H$_2$SO$_4$ | 100 | 220 |
| 2-4 | 30 | 120 | 13 | NH$_2$NH$_2$ + NH$_2$NH$_2$H$_2$SO$_4$ | 96 | 320 |
| 2-6 | 40 | 48 | 13 | NH$_2$NH$_2$ + NH$_2$NH$_2$H$_2$SO$_4$ | 96 | 260 |
| 2-8 | 40 | 120 | 13 | NH$_2$NH$_2$ + NH$_2$NH$_2$H$_2$SO$_4$ | 92 | 170 |
| 2-9 | 55 | 24 | 13 | NH$_2$NH$_2$ + NH$_2$NH$_2$H$_2$SO$_4$ | 93 | 60 |
| 2-10 | 55 | 48 | 13 | NH$_2$NH$_2$ + NH$_2$NH$_2$H$_2$SO$_4$ | 89 | 70 |
| 2-11 | 55 | 72 | 13 | NH$_2$NH$_2$ + NH$_2$NH$_2$H$_2$SO$_4$ | 83 | 40 |
| 2-12 | 55 | 120 | 13 | NH$_2$NH$_2$ + NH$_2$NH$_2$H$_2$SO$_4$ | 77 | 50 |

Example 3—Deacetylation of Hyaluronic Acid by Homogeneous Alkaline Hydrolysis—Comparative Example HA (1 000 kDa) was weighed to a reaction vessel, NaOH solution was added and the reaction was mixed until a homogenous solution was obtained. The mixture was incubated as set out in Table 3 without stirring and subsequently diluted with water and EtOH. The mixture was neutralized by adding 1.2 M HCl, precipitated by adding EtOH. The precipitate was washed with ethanol (70 w/w %) followed by ethanol and dried in vacuum overnight to obtain a solid. Deacetylation by homogeneous alkaline hydrolysis gives more degradation of the HA backbone, i.e. lower Mw of the deacetylated product as compared to hydroxylaminolysis (Example 1).

TABLE 3

| Example | Temp (° C.) | Time (h) | pH | Conditions | DoA (%) | Mw (SEC UV) (kDa) |
|---|---|---|---|---|---|---|
| 3-1 | 65 | 4 | 13 | 1M NaOH (aq.) | 99 | 10 |

Example 4—Deacetylation of Hyaluronic Acid by Heterogeneous Alkaline Hydrolysis—Comparative Example HA (1 000 kDa) was weighted to a reaction vessel and NaOH in EtOH (70% w/w %) was added as set out in Table 4. The heterogeneous mixture was incubated and subsequently neutralized by addition of 1.2 M HCl. The precipitate was washed with ethanol (75 w/w %) followed by ethanol and dried in vacuum overnight to obtain a solid.

Deacetylation by heterogeneous alkaline hydrolysis gives more degradation of the HA backbone, i.e. lower Mw of the deacetylated product as compared to hydroxylaminolysis (Example 1).

TABLE 4

| Example | Temp (° C.) | Time (h) | Conditions | DoA (%) | Mw (SEC UV) (kDa) |
|---|---|---|---|---|---|
| 4-1 | 35 | 24 | 1.0M NaOH (70% EtOH) | 99 | 60 |

Example 5—Crosslinking Deacetylated HA

The coupling agent DMTMM was dissolved in Na-phosphate buffer (pH 7.4), if needed pH was adjusted on the DMTMM mixture and the solution was subsequently added to deacetylated HA. The reaction mixture was homogenized by shaking for 3.5 minutes and mixing with a spatula or by pressing the mixture though a filter. The reaction mixture was placed in a water bath at 35° C. for 24 hours. The reaction was stopped by removal from the water bath and the gel was cut in to small pieces with a spatula or pressed through a filter. The reaction mixture was adjusted to pH>13 with 0.25 M NaOH, stirred for approx. 60 minutes and subsequently neutralized with 1.2 M HCl. After neutralization, the gels were precipitated in ethanol and washed with ethanol (70 w/w %) and dried in vacuum overnight. The dried gels were swelled in phosphate buffer in 0.7% NaCl for at least two hours. The pH was controlled and adjusted if necessary to 7.4. The gel particles were reduced in size with fine filter. The gel was filled in syringes and the syringes were sterilized by autoclavation. The results presented in Table 5 show formation of hydrogels by crosslinking deacetylated HA with different Mw and DoA, using DMTMM.

TABLE 5

| Example | Start Mw (kDa) | Start DoA (%) | DMTMM (mol %) | $SwCC_{PS}$ (mL/g) | GelP (%) | $CrD_{amide}$ |
|---|---|---|---|---|---|---|
| 5-1 | 110 | 82 | 2.3 | 256 | 54 | 0.5 |
| 5-2 | 110 | 82 | 2.6 | 127 | 67 | 0.5 |
| 5-3 | 160 | 89 | 0.9 | 150 | 68 | 0.2 |
| 5-4 | 160 | 89 | 1.2 | 95 | 74 | 0.2 |
| 5-5 | 240 | 93 | 1.25 | 137 | 71 | 0.4 |
| 5-6 | 240 | 93 | 1.5 | 89 | 80 | NA |
| 5-7 | 670 | 87 | 4.0 | 95 | 83 | 1.0 |
| 5-8 | 670 | 87 | 5.0 | 54 | 93 | 1.2 |
| 5-9 | 390 | 85 | 4.5 | 402 | 54 | 0.6 |
| 5-10 | 390 | 85 | 5.0 | 367 | 58 | 0.6 |
| 5-11 | 550 | 85 | 2.9 | 223 | 61 | 0.6 |
| 5-12 | 550 | 85 | 3.2 | 148 | 66 | 0.7 |
| 5-14 | 570 | 86 | 3.0 | 747 | 15 | 0.5 |
| 5-15 | 570 | 86 | 3.3 | 542 | 32 | 0.6 |
| 5-16 | 920 | 89 | 2.0 | 209 | 48 | 0.3 |

Example 6—Crosslinking a Mixture of Deacetylated HA and HA

HA and deacetylated HA was dissolved in 40 mL of water (Milli-Q) in a 50 mL Falcon tube with end-over-end stirring for 24 hours. After complete dissolution, the samples were freeze-dried. The coupling agent DMTMM was dissolved in Na-phosphate buffer (pH 7.4), pH was measured on the DMTMM mixture and was subsequently added to the freeze-dried mixture. The reaction mixture was homogenized and placed in a water bath at 35° C. for 24 hours. The reaction was stopped by removal from the water bath and the gel was cut in to small pieces with a spatula. The reaction mixture was adjusted to pH>13 with 0.25 M NaOH for about 60 minutes. The gels were neutralized with 1.2 M HCl. After neutralization, the gels were precipitated with ethanol and washed with ethanol (70%) and dried in vacuum overnight. The dried gels were swelled in phosphate buffer in 0.7% NaCl for at least two hours.

The pH was controlled and adjusted if necessary to 7.4. The gel particles were reduced in size with a fine filter. The gel was filled in syringes and the syringes were sterilized by autoclavation. The results presented in Table 5 show formation of hydrogels by crosslinking deacetylated HA with HA using DMTMM.

TABLE 6

| Ex | Start Mw DeAc HA (kDa) | Start DoA DeAc HA (%) | Start Mw HA (kDa) | HA/ deAcHA (%) | DMTMM (mol %) | $SwCC_{PS}$ (mL/g) | GelP (%) | $CrD_{amide}$ |
|---|---|---|---|---|---|---|---|---|
| 6-1 | 110 | 82 | 1000 | 50/50 | 1 | 385 | 39 | 0.4 |
| 6-2 | 110 | 82 | 1000 | 25/75 | 0.74 | 145 | 35 | 0.5 |

Example 7—Crosslinking a Mixture of HMW Deacetylated HA and LMW Deacetylated HA

Deacetylated HA of two different Mw were mixed together. The coupling agent DMTMM was dissolved in Na-phosphate buffer (pH 7.4), if needed pH was adjusted on the DMTMM mixture and the solution was subsequently added to the deacetylated HA. The reaction mixture was homogenized by mixing with a spatula or by pressing the mixture though a filter. The reaction mixture was placed in an incubator at 23° C. for 24 hours. The reaction was stopped by removal from the incubator and the gel was cut in to small pieces with a spatula or pressed through a filter. The reaction mixture was adjusted to pH>13 with 0.25 M NaOH, stirred for approx. 60 minutes and subsequently neutralized to pH 7.4 with 1.2 M HCl.

TABLE 7

| Ex | Start Mw LMW DeAc HA (kDa) | Start DoA LMW DeAc HA (%) | Start Mw HMW DeAc HA (kDa) | Start DoA HMW DeAc HA (%) | LMW/ HMW (%) | DMTMM (mol %) | SwF (mL/g) | G' (0.1 Hz; Pa) |
|---|---|---|---|---|---|---|---|---|
| 7-1 | 110 | 95 | 920 | 89 | 25/75 | 3 | 3 | 80 |

Example 8—Heterogeneous Re-Acetylation of a Hydrogel

The coupling agent DMTMM was dissolved in Na-phosphate buffer (pH 7.4), if needed pH was adjusted on the DMTMM mixture and the solution was subsequently added to deacetylated HA. The reaction mixture was homogenized by shaking for 3.5 minutes and mixing with a spatula or by pressing the mixture though a filter. The reaction mixture was placed in a water bath at 35° C. for 24 hours. The reaction was stopped by removal from the water bath and the gel was cut in to small pieces with a spatula or pressed through a filter. The reaction mixture was adjusted to pH>13 with 0.25 M NaOH, stirred for 60 minutes and subsequently neutralized with 1.2 M HCl. After neutralization, the gels were precipitated in ethanol and washed with ethanol (70 w/w %) and dried in vacuum overnight.

The precipitated gel was suspended in MeOH and Ac$_2$O (20 equiv./HA disaccharide) was added. The suspension was incubated at 40° C. for 24 hrs followed by filtration, the obtained solid was washed with 70 w/w % EtOH, washed with EtOH and subsequently dried in vacuum overnight. The acetylated gel was dissolved in 0.25 M NaOH, stirred for 60 minutes and subsequently neutralized with 1.2 M HCl. After neutralization, the gels were precipitated in ethanol and washed with ethanol (70 w/w %) and dried in vacuum overnight. The dried gels were swelled in phosphate buffer in 0.7% NaCl for at least two hours.

As a control experiment (example 8-3), HA (310 kDa) was suspended in MeOH and Ac$_2$O (20 equiv/HA disaccharide) was added. The suspension was incubated at 40° C. for 24 hrs followed by filtration, the obtained solid was washed with 70 w/w % EtOH, with EtOH and subsequently dried in vacuum overnight. The product was dissolved in 0.25 M NaOH, stirred for 60 minutes and subsequently neutralized with 1.2 M HCl. After neutralization, the gels were precipitated in ethanol and washed with ethanol (70 w/w %) and dried in vacuum overnight. Mw of the obtained product was analyzed. The results are summarized in Table 8.

TABLE 8

| Ex | Start Mw (kDa) | Start DoA (%) Crosslinking reaction | DMTMM (mol %) | DoA (%) Gel powder Precipitated gel before acetylation | [PS] (mg/mL) | GelP (%) | SwCC$_{PS}$ (mL/g) | DoA (%) after acetylation | Mw SEC-UV (kDa) |
|---|---|---|---|---|---|---|---|---|---|
| | | | | | | | Gel after acetylation | | |
| 8-1 | 240 | 93 | 1.3 | 94 | 29 | 79 | 126 | 98 | NA |
| 8-2 | 110 | 82 | 2.7 | 84 | 29 | 91 | 60 | 95 | NA |
| 8-3 | 310 | NA | NA | NA | NA | NA | NA | NA | 220 |

Example 9—Homogeneous Re-Acetylation of a Hydrogel

The coupling agent DMTMM was dissolved in Na-phosphate buffer (pH 7.4), and pH was controlled and adjusted if necessary. The DMTMM solution was subsequently added to deacetylated HA. The suspension was homogenized by shaking for 3.5 minutes and mixing with a spatula or by pressing the mixture though a filter. The reaction mixture was placed in an incubator at 23° C. for 24 hours. The reaction was stopped by removal from the incubator and the gel was mixed with spatula or pressed through a 1 mm steel mesh two times. Followed by addition of 0.25 M NaOH to the resulting material (pH>13) and mixed for 60 minutes and subsequently neutralized with 1.2 M HCl. After neutralization, the gels particle-size reduced through a fine filter. Then, the gels were precipitated in EtOH and washed with 70 w/w % EtOH and EtOH. The resulting material was dried in vacuum overnight.

The precipitated gel powder was added to deionised water and left to mix for 60 minutes. Triethanolamine (1.5 equiv./HA disaccharide) and Ac$_2$O (1 equiv./HA disaccharide) were added to the gel suspension. The reaction mixture was mixed at 23° C. for 60 minutes. Followed by addition of 0.25 M NaOH to the acetylated gel (pH>13), mixed for 45 minutes and subsequently neutralized with 1.2 M HCl. After neutralization, the gel was precipitated in EtOH and washed with 70 w/w % EtOH+100 mM NaCl, 70 w/w % EtOH followed by EtOH and dried in vacuum overnight. The dried gel was swelled in Na-phosphate buffer at room temperature for at least two hours and then particle-size reduced through a fine filter.

As a control experiment (example 9-3), deacetylated HA (1 700 kDa) was added to deionised water and left to mix for 60 minutes. Triethanolamine (1.2 equiv./HA disaccharide) and Ac$_2$O (1 equiv./HA disaccharide) were added to the HA mixture. The reaction mixture was mixed at 23° C. for 60 minutes followed by addition of 0.25 M NaOH (pH>13), mixed for 40 minutes and subsequently neutralized with 1.2 M HCl. After neutralization, the mixture was precipitated in EtOH and washed with 70 w/w % EtOH+100 mM NaCl, 70 w/w % EtOH followed by EtOH and dried in vacuum overnight. Mw and DoA of the obtained product was analyzed. The results are summarized in Table 9.

TABLE 9

| Ex | Start Mw (kDa) | Start DoA (%) Crosslinking reaction | DMTMM (mol %) | DoA (%) Gel powder Precipitated gel before acetylation | [PS] (mg/mL) | GelP (%) | SwCC$_{PS}$ (mL/g) | DoA (%) after acetylation | Mw SEC-UV (kDa) |
|---|---|---|---|---|---|---|---|---|---|
| | | | | | | | Gel after acetylation | | |
| 9-1 | 1700 | 95 | 2.4 | 95 | 22 | 70 | 115 | 100 | NA |
| 9-2 | 1700 | 95 | 2.7 | 95 | 21 | 59 | 165 | 100 | NA |
| 9-3 | 1700 | 95 | NA | NA | NA | NA | NA | 99 | 1500 |

Example 10—Alkaline Hydrolysis of Crosslinked HA Gel

The coupling agent DMTMM was dissolved in Na-phosphate buffer (pH 7.4), if needed, the pH was adjusted on the DMTMM mixture and the solution was subsequently added to deacetylated HA. The reaction mixture was homogenized by shaking for 3.5 minutes and mixing with a spatula or by pressing the mixture though a filter. The reaction mixture was placed in a water bath at 35° C. for 24 hours. The reaction was stopped by removal from the water bath and the gel was cut in to small pieces with a spatula or pressed through a filter.

The gel was divided in two parts, for one part of the gel the pH was adjusted to pH>13 with 0.25 M NaOH and was stirred about 60 minutes and subsequently neutralized with 1.2 M HCl. After neutralization, the gels were precipitated in ethanol and washed with ethanol (70 w/w %) followed by ethanol and dried in vacuum overnight. If decided, the dried gel was swelled in phosphate buffer in 0.7% NaCl at room temperature for at least two hours and then particle-size reduced through a fine filter. The gel pH was controlled and adjusted to 7.2-7.5 if needed.

The second part of the gel was diluted with water and pH was adjusted to 6.5-7.5. After neutralization, the gels were precipitated with ethanol and washed with ethanol (70 w/w %) followed by ethanol and dried in vacuum overnight. If decided, the dried gel was swelled in phosphate buffer in 0.7% NaCl at room temperature for at least two hours and then particle-size reduced through a fine filter. The gel pH was controlled and adjusted to 7.2-7.5 if needed. The alkaline treatment is done to hydrolyze inter- and intramolecular ester bonds formed between HA chains during the crosslinking step, and potential O-acetates and anhydrides formed during the re-acetylation step as well as residual active esters formed by the coupling reagent. The alkaline hydrolysis results in exclusively amide bonds in the material.

As a control experiment (example 10-13 to 10-15, table 10.3), HA was added to Na-phosphate buffer (pH 7.4). The reaction mixture was homogenized by shaking for 3.5 minutes and pressing the mixture though a filter. The reaction mixture was placed in a water bath at 5, 35 or 50° C. for 24 hours. The reaction was stopped by removal from the water bath and the mixture was pressed through a filter. The mixture was adjusted to pH>13 with 0.25 M NaOH for 60-100 minutes. The mixture was neutralized with 1.2 M HCl. After neutralization, HA was precipitated with ethanol and washed with ethanol (70%), washed with ethanol and dried in vacuum overnight. Mw of the obtained product was analyzed. The results summarized in Tables 10.1-10.3 show that post-crosslinking alkaline treatment gives the gel increased swelling properties and lower CrD.

TABLE 10.1

| Ex. | Start Mw (kDa) | Start DoA (%) | DMTMM (mol %) | Time (min) | SwC (mL/g) | SwCC$_{PS}$ | GelP (%) | [PS] (mg/mL) |
|---|---|---|---|---|---|---|---|---|
| 10-1 | 240 | 95 | 25 | 0 | 14 | NA | NA | NA |
| 10-2 | 240 | 95 | 25 | 60 | 18 | NA | NA | NA |
| 10-3 | 100 | 82 | 2.6 | 0 | NA | 55 | 91 | 50 |
| 10-4 | 100 | 82 | 2.6 | 60 | NA | 79 | 82 | 46 |
| 10-5 | 670 | 87 | 6.0 | 0 | 23 | NA | NA | NA |
| 10-6 | 670 | 87 | 6.0 | 60 | 35 | NA | NA | NA |
| 10-7 | 670 | 87 | 7.9 | 0 | 19 | NA | NA | NA |
| 10-8 | 670 | 87 | 7.9 | 60 | 27 | NA | NA | NA |

TABLE 10.2

| Ex. | Start Mw (kDa) | Start DoA (%) | DMTMM (mol %) | Time (min) | CrD* |
|---|---|---|---|---|---|
| 10-9 | 1700 | 95 | 2.4 | 0 | 0.34 |
| 10-10 | 1700 | 95 | 2.4 | 60 | 0.30 |
| 10-11 | 950 | 89 | 4.0 | 0 | 0.88 |
| 10-12 | 950 | 89 | 4.0 | 60 | 0.73 |

*CrD for non-alkaline treated gels in table 10.2 also includes ester crosslinks.

TABLE 10.3

| Ex. | Start Mw (kDa) | Temp (° C.) | Time (min) | Final Mw (kDa) |
|---|---|---|---|---|
| 10-13 | 1360 | 5 | 100 | 1340[b] |
| 10-14 | 920 | 35 | 60 | 860[a] |
| 10-15 | 1360 | 50 | 70 | 1230[b] |

[a]SEC-UV
[b]SEC-MALS

Example 11—Preparation of N-((2R,3R,4S)-1,3,4,5-tetrahydroxy-6-(trityloxy)hexan-2-yl)acetamide A solution of N-((2R,3S,5S)-2,4,5-trihydroxy-6-trityloxymethyl-tetrahydro-pyran-3-yl)-acetamide (556 mg, 1.20 mol, 1.00 eq.) in a mixture of THF-H$_2$O (20 ml, 4:1) at r.t., was treated with solid sodium borohydride (49.92 mg, 1.32 mol, 1.10 eq.) [gas evolution]. The reaction mixture was stirred at r.t. for 2 h, concentrated to dryness to afford N-((2R,3R,4S)-1,3,4,5-tetrahydroxy-6-(trityloxy)hexan-2-yl)acetamide (500 mg, 89.54%) as a white solid that was used without further purification.

LCMS: t$_R$=1.01 min., purity=100%; ES+, 464.26 (M−H)⁻.

Example 12—Deacetylation of N-((2R,3R,4S)-1,3,4,5-tetrahydroxy-6-(trityloxy)hexan-2-yl)acetamide A suspension of N-((2R,3R,4S)-1,3,4,5-tetrahydroxy-6-(trityloxy)hexan-2-yl)acetamide (1 eq) in hydroxylamine (10 volumes) was either treated with acid additives to lower the pH to 7 or not as set out in Table 11, Examples 12-1 to 12-9. The mixture was heated at 80° C. until full conversion of the deacetylation was reached. Deacetylation of N-((2R,3R,4S)-1,3,4,5-tetrahydroxy-6-(trityloxy)hexan-2-yl)acetamide with hydrazine (pH 13) under the same conditions as in Example 2 is also included as Example 13-10.

The results are displayed in Table 11. The results show that the deacetylation procedure proceeds considerably faster with hydroxylamine than with hydrazine, and is significantly by the addition of a pH reducing agent.

TABLE 11

| Example | Solvent (50 vols)* | Additive | pH | Time to reach 100% conversion |
|---|---|---|---|---|
| 12-1 | 50% NH$_2$OH (aq) | None | 10.2 | 72 h |
| 12-2 | 50% NH$_2$OH (aq) | HCl | 7 | 12 h |
| 12-3 | 50% NH$_2$OH (aq) | HBr | 7 | 9 h |
| 12-4 | 50% NH$_2$OH (aq) | HI | 7 | 5 h |
| 12-5 | 50% NH$_2$OH (aq) | H$_2$SO$_4$ | 7 | 29 h |
| 12-6 | 50% NH$_2$OH (aq) | CH$_3$COOH | 7 | 6 h |
| 12-7 | 50% NH$_2$OH (aq) | TFA | 7 | 4 h |
| 12-8 | 50% NH$_2$OH (aq) | (CH$_3$)$_3$COOH | 7 | 5 h |
| 12-9 | 50% NH$_2$OH (aq) | CH$_3$CH$_2$COOH | 7 | 8 h |
| 12-10 | NH$_2$NH$_2$·H$_2$O | None | 13 | 120 h |

The reaction mixtures were purified directly by Preparative LCMS to afford (2R,3R,4S)-2-amino-6-(trityloxy)hexane-1,3,4,5-tetraol as a white solid.

LCMS: t$_R$=0.88 min., purity=99%; ES+, 422.11 (M−H)⁻.

¹H NMR (DMSO-d$_6$) δ: 7.47-7.37 (m, 6H), 7.30 (dd, J=8.3, 6.7 Hz, 6H), 7.26-7.15 (m, 3H), 3.92 (m, 1H), 3.83-3.74 (m, 1H), 3.62-3.53 (m, 1H), 3.52-3.41 (m, 1H), 3.34-3.27 (m, 1H), 3.22-3.16 (m, 1H), 3.13-3.04 (m, 1H), 3.01-2.91 (m, 1H)

Example 13—Preparation of N-(4-aminophenethyl)acetamide

A 4-(2-aminoethyl)aniline (1.50 g; 11.01 mmol; 1.00 eq.) was added neat p-cresyl acetate (1.65 g, 11.0 mmol, 1.00 eq.) and the reaction mixture was stirred at room temperature for 30 h. The resulting orange solution was absorbed directly on silica gel and purified by flash chromatography (silica gel, DCM/MeOH 0-5%) to afford N-(4-aminophenethyl)acetamide (1.76 g, 89.7% yield)

LCMS: t$_R$=0.58 min., purity=99.5%; ES+, 179.5 (M+H)⁺.

¹H-NMR (400 MHz, DMSO-d$_6$) δ 1.78 (s, 3H), 2.50 (m, 2H hidden by DMSO signal) 3.14 (m, 2H), 4.83 (s, 2H), 6.49 (d, J=7.5 Hz, 2H), 6.84 (d, J=7.5 Hz, 2H), 7.82 (s, 1H).

Example 14—Preparation of tert-butyl (4-(2-acetamidoethyl)phenyl)carbamate

To a stirred solution of N-[2-(4-Amino-phenyl)-ethyl]-acetamide (500 mg, 2.81 mmol, 1.00 eq.) in DCM (20 ml) at r.t., was added triethylamine (0.51 ml, 3.65 mmol, 1.30 eq.) followed by di-tert-butyl dicarbonate (673.48 mg, 3.09 mmol, 1.10 eq.). The reaction mixture is stirred at r.t. for 1 h, washed with water (5 ml), a saturated solution of NaHSO$_4$ (aq) (5 ml) and water (3×5 ml), dried over MgSO$_4$ and concentrated to dryness to afford tert-butyl (4-(2-acetamidoethyl)phenyl)carbamate (496 mg, 63% yield) as a pale orange solid.

LCMS: t$_R$=1.11 min., purity=100%; ES+, 279.5 (M+H).

¹H-NMR (DMSO-d$_6$) δ 1H NMR (400 MHz, DMSO-d6) δ 1.57 (s, 9H), 1.87 (s, 3H), 2.75-2.64 (m, 2H), 3.36-3.20 (m, 2H), 7.27-7.07 (m, 2H), 7.45 (d, J=8.3 Hz, 2H), 7.94 (t, J=5.6 Hz, 1H), 9.31 (s, 1H).

Example 15—Preparation of NH$_2$OH·HI

To a stirred solution of 50% NH$_2$OH (aq) (9.28 ml, 0.15 mol, 1.00 eq) at 0° C. was added carefully dropwise 57% HI (aq) over a period of 5 minutes until a pH of 7 was achieved. A dense white crystalline solid formed that was collected by filtration, washed carefully with ice cold water to afford hydroxylamine hydrogen iodide (6.80 g, 28%).

Example 16—Preparation of NH$_2$OH·TFA

To a stirred solution of 50% NH$_2$OH (aq) (9.28 ml, 0.15 mol, 1.00 eq) at 0° C. was added carefully dropwise TFA over a period of 5 minutes until a pH of 7 was achieved. The reaction mixture was concentrated under nitrogen sparging to afford hydroxylamine·trifluoroacetate (11.0 g, 98%) as clear colourless oil.

Example 17—Comparative Studies of NH$_2$OH and Salts Thereof Versus Commonly Used Transamidation Agents Such as NH$_2$NH$_2$·H$_2$O and NaOH -continued To a stirred solution/suspension of tert-butyl (4-(2-acetamidoethyl)phenyl)-carbamate (50 mg, 0.18 mmol) in the chosen solvent (5 volumes) was added the salt (5 eq) and the resulting mixture was heated at 80° C. for the time necessary to complete the reaction. The results are summarized in Table 12.

LCMS: $t_R$=0.81 min., purity=100%; ES+, 237.51 (M+H)$^+$.

$^1$H-NMR (DMSO-d$_6$) δ 1H NMR (400 MHz, DMSO-d$_6$) δ 9.26 (s, 1H), 8.40 (s, 1H), 7.38 (d, J=8.0 Hz, 2H), 7.11 (d, J=8.0 Hz, 2H), 2.89 (m, 2H), 2.80-2.63 (m, 2H), 1.47 (s, 9H) (isolated as formate salt).

TABLE 12

| Example | Solvent (5 vols)* | Additive | pH | 1 h (% conv.) | 2 h (% conv.) | 4 h (% conv.) |
|---|---|---|---|---|---|---|
| 17-1 | 50% NH$_2$OH (aq) | None | 10.2 | 34.8 | 64.7 | 83.0 |
| 17-2 | 50% NH$_2$OH (aq) | 5 eq NH$_2$OH•HI | 9 | 48.6 | 83.5 | 97.0 |
| 17-3 | EtOH/H$_2$O (4:1) | 5 eq NH$_2$OH•HI | 7 | 63.8 | 85.8 | 98.9 |
| 17-4 | NH$_2$NH$_2$•H$_2$O | None | 13 | 13.6 | 34.9 | 35.2 |
| 17-5 | NH$_2$NH$_2$•H$_2$O | 5 eq NH$_2$OH•HI | 13 | 57.9 | 86.9 | 97.4 |
| 17-6 | EtOH (4 vols) | 4N NaOH (aq) (1 vol) | 14 | 3.7 | 11.63 | 14.5 |
| 17-7 | EtOH/H$_2$O (4:1) | 5 eq NH$_2$OH•HCl | 7 | 3.4 | 5.8 | 17.2 |
| 17-8 | EtOH/H$_2$O (4:1) | 5 eq NH$_2$OH•H$_2$SO$_4$ | 7 | 0 | 0.2 | 0.7 |
| 17-9 | EtOH/H$_2$O (4:1) | 5 eq NH$_2$OH•TFA | 7 | 34.2 | 72.4 | 91.3 |
| 17-10 | EtOH/H$_2$O (4:1) | 5 eq NH$_4$I | 7 | 0 | 0 | 0 |

*Volume = 1 g = 1 ml = 1 volume

The invention claimed is:

1. A hydrogel product comprising acylated crosslinked glycosaminoglycans (GAGs), produced by a method comprising:
crosslinking (i) an at least partially deacetylated GAG comprising free amine groups and (ii) a second GAG comprising activated carboxyl groups, by forming amide bonds between 2'-amino groups on the at least partially deacetylated GAG and the activated carboxyl groups of the second GAG,
wherein the hydrogel product has residual free amine groups and a degree of acetylation of at least 95%.

2. The hydrogel product according to claim 1, wherein the at least partially deacetylated GAG is selected from the group consisting of deacetylated hyaluronic acid, deacetylated chondroitin, and deacetylated chondroitin sulfate, and mixtures thereof.

3. The hydrogel product according to claim 2, wherein the at least partially deacetylated GAG is deacetylated hyaluronic acid.

4. The hydrogel product according to claim 1, wherein the at least partially deacetylated GAG has a degree of acetylation of 95% or less, and a weight average molecular weight of 0.1 MDa or more.

5. The hydrogel product according to claim 1, wherein the at least partially deacetylated GAG is prepared by:
(a) allowing a GAG comprising N-acetyl groups to react with hydroxylamine (NH$_2$OH), or a salt thereof, at a temperature of 100° C. or less for 2-200 hours to form the at least partially deacetylated GAG, and
(b) recovering the at least partially deacetylated GAG.

6. The hydrogel product according to claim 1, wherein the second GAG is selected from the group consisting of hyaluronic acid, chondroitin, and chondroitin sulfate, and mixtures thereof.

7. The hydrogel product according to claim 6, wherein the second GAG is hyaluronic acid.

8. The hydrogel product according to claim 1, wherein the activated carboxyl groups on the second GAG are formed using a coupling agent.

9. The hydrogel product according to claim 8, wherein the coupling agent is a peptide coupling reagent.

10. The hydrogel product according to claim 8, wherein the coupling reagent is DMTMM.

11. The hydrogel product according to claim 1, wherein the method of producing the acylated crosslinked GAGs further comprises acetylating residual free amine groups of the crosslinked GAGs.

12. The hydrogel product according to claim 1, wherein the method of producing the acylated crosslinked GAGs further comprises hydrolyzing ester crosslinks formed as byproducts during the crosslinking by subjecting the crosslinked acetylated GAGs to alkaline solution.

13. The hydrogel product according to claim 12, wherein the alkaline solution comprises sodium hydroxide or potassium hydroxide.

14. The hydrogel product according to claim 13, wherein the hydrolyzing is performed in sodium hydroxide solution at a pH of 12 to 14, for 0.5 to 4 hours.

15. The hydrogel product according to claim 1, wherein the hydrogel product is in a solid, dry form.

16. The hydrogel product according to claim 1, wherein the at least partially deacetylated GAG has a weight average molecular weight of 0.5 MDa or more.

17. The hydrogel product according to claim 1, wherein the crosslinked GAGs are substantially free of ester crosslinks.

18. The hydrogel product according to claim 1, wherein the crosslinked GAGs comprise two different GAGs selected from hyaluronic acid, chondroitin, chondroitin sulphate, heparin sulphate, heparosan, heparin, dermatan sulphate, and keratin sulphate.

19. The hydrogel product according to claim 1, wherein the second GAG is non-deacetylated.

20. A composition comprising:
the hydrogel product according to claim 1; and
water.

* * * * *